(12) United States Patent
Baum

(10) Patent No.: US 6,512,095 B2
(45) Date of Patent: Jan. 28, 2003

(54) MOLECULES DESIGNATED B7L-1

(75) Inventor: Peter R. Baum, Seattle, WA (US)

(73) Assignee: Immunex Corp., Seattle, WA (US)

( * ) Notice: Subject to any disclaimer, the term of this patent is extended or adjusted under 35 U.S.C. 154(b) by 0 days.

(21) Appl. No.: 09/778,510

(22) Filed: Feb. 6, 2001

(65) Prior Publication Data

US 2002/0164686 A1 Nov. 7, 2002

Related U.S. Application Data

(63) Continuation of application No. PCT/US99/17906, filed on Aug. 5, 1999.
(60) Provisional application No. 60/095,663, filed on Aug. 7, 1998, now abandoned.

(51) Int. Cl.[7] .................. C07K 14/705; C07K 16/46; A61K 38/17; A61K 39/00
(52) U.S. Cl. .............. 530/350; 530/387.1; 530/387.3; 530/395; 424/130.1; 424/133.1; 424/134.1; 424/184.1; 424/185.1; 424/192.1; 424/193.1; 514/2; 514/8
(58) Field of Search .................. 530/350, 387.3, 530/387.1, 395; 514/2, 8; 424/184.1, 185.1, 192.1, 134.1, 133.1, 130.1, 193.1

(56) References Cited

U.S. PATENT DOCUMENTS 6,218,510 B1    4/2001  Sharpe et al.

FOREIGN PATENT DOCUMENTS

| CN | 1242376 A | 1/2000 |
|---|---|---|
| EP | 0 939 124 A3 | 9/1999 |
| WO | WO 98/44113 | 10/1998 |
| WO | WO 98/54963 | 12/1998 |
| WO | WO 99/14328 | 3/1999 |
| WO | WO 00/32633 | 6/2000 |
| WO | WO 00/53753 | 9/2000 |

OTHER PUBLICATIONS

Attwood Science 290(5491):471–473, Oct. 27, 2000.*

Hillier L, et al. Database Genbank 'Online' Accession No. R88252, "ym90f09.r1 Soares adult brain N2b4HB55Y Homo sapiens cDNA clone IMAGE: 166217 5', mRNA sequence,"Aug. 16, 1995.

* cited by examiner

Primary Examiner—Phillip Gambel
Assistant Examiner—Jessica H. Roark
(74) Attorney, Agent, or Firm—Paul B. Tran; Joseph R. Baker; Julie K. Smith

(57) ABSTRACT

The invention is directed to B7L-1 as a purified and isolated protein, the DNA encoding the B7L-1, host cells transfected with cDNAs encoding B7L-1 and processes for preparing B7L-1 polypeptides.

27 Claims, No Drawings

SEQUENCE LISTING

<160> NUMBER OF SEQ ID NOS:    22

<210> SEQ ID NO 1
<211> LENGTH: 1820
<212> TYPE: DNA
<213> ORGANISM: Homo sapien
<220> FEATURE:
<221> NAME/KEY: CDS
<222> LOCATION: 157..1452

<400> SEQUENCE: 1

```
aagcttggca cgaggcggtc cccacctcgg ccccgggctc cgaagcggct cggggcgcc        60 ctttcggtca acatcgtagt ccacccctc cccatcccca gccccgggg attcaggctc       120 gccagcgccc agccagggag ccggccggga agcgcg atg ggg gcc cca gcc gcc       174
                                        Met Gly Ala Pro Ala Ala
                                         1               5 tcg ctc ctg ctc ctg ctc ctg ctg ttc gcc tgc tgc tgg gcg ccc ggc       222
Ser Leu Leu Leu Leu Leu Leu Leu Phe Ala Cys Cys Trp Ala Pro Gly
             10                  15                  20 ggg gcc aac ctc tcc cag gac ggc tac tgg cag gag cag gat ttg gag       270
Gly Ala Asn Leu Ser Gln Asp Gly Tyr Trp Gln Glu Gln Asp Leu Glu
         25                  30                  35 ctg gga act ctg gct cca ctc gac gag gcc atc agc tcc aca gtc tgg       318
Leu Gly Thr Leu Ala Pro Leu Asp Glu Ala Ile Ser Ser Thr Val Trp
     40                  45                  50 agc agc cct gac atg ctg gcc agt caa gac agc cag ccc tgg aca tct       366
Ser Ser Pro Asp Met Leu Ala Ser Gln Asp Ser Gln Pro Trp Thr Ser
 55                  60                  65                  70 gat gaa aca gtg gtg gct ggt ggc acc gtg gtg ctc aag tgc caa gtg       414
```

```
                Asp Glu Thr Val Val Ala Gly Gly Thr Val Val Leu Lys Cys Gln Val
                                 75                  80                  85 aaa gat cac gag gac tca tcc ctg caa tgg tct aac cct gct cag cag         462
Lys Asp His Glu Asp Ser Ser Leu Gln Trp Ser Asn Pro Ala Gln Gln
             90                  95                 100 act ctc tac ttt ggg gag aag aga gcc ctt cga gat aat cga att cag         510
Thr Leu Tyr Phe Gly Glu Lys Arg Ala Leu Arg Asp Asn Arg Ile Gln
            105                 110                 115 ctg gtt acc tct acg ccc cac gag ctc agc atc agc atc agc aat gtg         558
Leu Val Thr Ser Thr Pro His Glu Leu Ser Ile Ser Ile Ser Asn Val
        120                 125                 130 gcc ctg gca gac gag ggc gag tac acc tgc tca atc ttc act atg cct         606
Ala Leu Ala Asp Glu Gly Glu Tyr Thr Cys Ser Ile Phe Thr Met Pro
135                 140                 145                 150 gtg cga act gcc aag tcc ctc gtc act gtg cta gga att cca cag aag         654
Val Arg Thr Ala Lys Ser Leu Val Thr Val Leu Gly Ile Pro Gln Lys
                155                 160                 165 ccc atc atc act ggt tat aaa tct tca tta cgg gaa aaa gac aca gcc         702
Pro Ile Ile Thr Gly Tyr Lys Ser Ser Leu Arg Glu Lys Asp Thr Ala
            170                 175                 180 acc cta aac tgt cag tct tct ggg agc aag cct gca gcc cgg ctc acc         750
Thr Leu Asn Cys Gln Ser Ser Gly Ser Lys Pro Ala Ala Arg Leu Thr
        185                 190                 195 tgg aga aag ggt gac caa gaa ctc cac gga gaa cca acc cgc ata cag         798
Trp Arg Lys Gly Asp Gln Glu Leu His Gly Glu Pro Thr Arg Ile Gln
200                 205                 210 gaa gat ccc aat ggt aaa acc ttc act gtc agc agc tcg gtg aca ttc         846
Glu Asp Pro Asn Gly Lys Thr Phe Thr Val Ser Ser Ser Val Thr Phe
215                 220                 225                 230 cag gtt acc cgg gag gat gat ggg gcg agc atc gtg tgc tct gtg aac         894
Gln Val Thr Arg Glu Asp Asp Gly Ala Ser Ile Val Cys Ser Val Asn
                235                 240                 245 cat gaa tct cta aag gga gct gac aga tcc acc tct caa cgc att gaa         942
His Glu Ser Leu Lys Gly Ala Asp Arg Ser Thr Ser Gln Arg Ile Glu
            250                 255                 260 gtt tta tac aca cca act gcg atg att agg cca gac cct ccc cat cct         990
Val Leu Tyr Thr Pro Thr Ala Met Ile Arg Pro Asp Pro Pro His Pro
        265                 270                 275 cgt gag ggc cag aag ctg ttg cta cac tgt gag ggt cgc ggc aat cca        1038
Arg Glu Gly Gln Lys Leu Leu Leu His Cys Glu Gly Arg Gly Asn Pro
280                 285                 290 gtc ccc cag cag tac cta tgg gag aag gag ggc agt gtg cca ccc ctg        1086
Val Pro Gln Gln Tyr Leu Trp Glu Lys Glu Gly Ser Val Pro Pro Leu
295                 300                 305                 310 aag atg acc cag gag agt gcc ctg atc ttc cct ttc ctc aac aag agt        1134
Lys Met Thr Gln Glu Ser Ala Leu Ile Phe Pro Phe Leu Asn Lys Ser
                315                 320                 325 gac agt ggc acc tac ggc tgc aca gcc acc agc aac atg ggc agc tac        1182
Asp Ser Gly Thr Tyr Gly Cys Thr Ala Thr Ser Asn Met Gly Ser Tyr
            330                 335                 340 aag gcc tac tac acc ctc aat gtt aat gac ccc agt ccg gtg ccc tcc        1230
Lys Ala Tyr Tyr Thr Leu Asn Val Asn Asp Pro Ser Pro Val Pro Ser
        345                 350                 355 tcc tcc agc acc tac cac gcc atc atc ggt ggg atc gtg gct ttc att        1278
Ser Ser Ser Thr Tyr His Ala Ile Ile Gly Gly Ile Val Ala Phe Ile
360                 365                 370 gtc ttc ctg ctc ctc atc atg ctc atc ttc ctt ggc cac tac ttg atc        1326
Val Phe Leu Leu Leu Ile Met Leu Ile Phe Leu Gly His Tyr Leu Ile
375                 380                 385                 390
```

-continued

```
cgg cac aaa gga acc tac ctg aca cat gag gca aaa ggc tcc gac gat   1374
Arg His Lys Gly Thr Tyr Leu Thr His Glu Ala Lys Gly Ser Asp Asp
            395                 400                 405 gct cca gac gcg gac acg gcc atc atc aat gca gaa ggc ggg cag tca   1422
Ala Pro Asp Ala Asp Thr Ala Ile Ile Asn Ala Glu Gly Gly Gln Ser
        410                 415                 420 gga ggg gac gac aag aag gaa tat ttc atc tagaggcgcc tgcccacttc     1472
Gly Gly Asp Asp Lys Lys Glu Tyr Phe Ile
    425                 430 ctgcgccccc caggggccct gtggggactg ctggggccgt caccaacccg gacttgtaca  1532
gagcaaccgc agggccgccc ctcccgcttg ctccccagcc cacccacccc cctgtacaga  1592
atgtctgctt tgggtgcggt tttgtactcg gtttggaatg ggagggagg agggcggggg   1652 gaggggaggg ttgccctcag cccttccgt ggcttctctg catttgggtt attattattt   1712
ttgtaacaat cccaaatcaa atctgtctcc aggctggaga ggcaggagcc ctggggtgag  1772
aaaagcaaaa aacaaacaaa aaaaaaaaaa aaaaattcct gcggccgc              1820
```

<210> SEQ ID NO 2
<211> LENGTH: 432
<212> TYPE: PRT
<213> ORGANISM: Homo sapien

<400> SEQUENCE: 2

```
Met Gly Ala Pro Ala Ser Leu Leu Leu Leu Leu Leu Leu Leu Phe Ala
 1               5                  10                  15

Cys Cys Trp Ala Pro Gly Gly Ala Asn Leu Ser Gln Asp Gly Tyr Trp
            20                  25                  30

Gln Glu Gln Asp Leu Glu Leu Gly Thr Leu Ala Pro Leu Asp Glu Ala
        35                  40                  45

Ile Ser Ser Thr Val Trp Ser Ser Pro Asp Met Leu Ala Ser Gln Asp
    50                  55                  60

Ser Gln Pro Trp Thr Ser Asp Glu Thr Val Val Ala Gly Gly Thr Val
65                  70                  75                  80

Val Leu Lys Cys Gln Val Lys Asp His Glu Asp Ser Ser Leu Gln Trp
                85                  90                  95

Ser Asn Pro Ala Gln Gln Thr Leu Tyr Phe Gly Glu Lys Arg Ala Leu
            100                 105                 110

Arg Asp Asn Arg Ile Gln Leu Val Thr Ser Thr Pro His Glu Leu Ser
        115                 120                 125

Ile Ser Ile Ser Asn Val Ala Leu Ala Asp Glu Gly Glu Tyr Thr Cys
    130                 135                 140

Ser Ile Phe Thr Met Pro Val Arg Thr Ala Lys Ser Leu Val Thr Val
145                 150                 155                 160

Leu Gly Ile Pro Gln Lys Pro Ile Ile Thr Gly Tyr Lys Ser Ser Leu
                165                 170                 175

Arg Glu Lys Asp Thr Ala Thr Leu Asn Cys Gln Ser Ser Gly Ser Lys
            180                 185                 190

Pro Ala Ala Arg Leu Thr Trp Arg Lys Gly Asp Gln Glu Leu His Gly
        195                 200                 205

Glu Pro Thr Arg Ile Gln Glu Asp Pro Asn Gly Lys Thr Phe Thr Val
    210                 215                 220

Ser Ser Ser Val Thr Phe Gln Val Thr Arg Glu Asp Asp Gly Ala Ser
225                 230                 235                 240

Ile Val Cys Ser Val Asn His Glu Ser Leu Lys Gly Ala Asp Arg Ser
                245                 250                 255
```

-continued

```
Thr Ser Gln Arg Ile Glu Val Leu Tyr Thr Pro Thr Ala Met Ile Arg
        260                 265                 270

Pro Asp Pro Pro His Pro Arg Glu Gly Gln Lys Leu Leu Leu His Cys
        275                 280                 285

Glu Gly Arg Gly Asn Pro Val Pro Gln Gln Tyr Leu Trp Glu Lys Glu
        290                 295                 300

Gly Ser Val Pro Pro Leu Lys Met Thr Gln Glu Ser Ala Leu Ile Phe
305                 310                 315                 320

Pro Phe Leu Asn Lys Ser Asp Ser Gly Thr Tyr Gly Cys Thr Ala Thr
                325                 330                 335

Ser Asn Met Gly Ser Tyr Lys Ala Tyr Tyr Thr Leu Asn Val Asn Asp
            340                 345                 350

Pro Ser Pro Val Pro Ser Ser Ser Thr Tyr His Ala Ile Ile Gly
        355                 360                 365

Gly Ile Val Ala Phe Ile Val Phe Leu Leu Leu Ile Met Leu Ile Phe
    370                 375                 380

Leu Gly His Tyr Leu Ile Arg His Lys Gly Thr Tyr Leu Thr His Glu
385                 390                 395                 400

Ala Lys Gly Ser Asp Asp Ala Pro Asp Ala Asp Thr Ala Ile Ile Asn
                405                 410                 415

Ala Glu Gly Gly Gln Ser Gly Gly Asp Asp Lys Lys Glu Tyr Phe Ile
            420                 425                 430

<210> SEQ ID NO 3
<211> LENGTH: 1273
<212> TYPE: DNA
<213> ORGANISM: Mus musculus
<220> FEATURE:
<221> NAME/KEY: CDS
<222> LOCATION: 13..1206

<400> SEQUENCE: 3
gtcgacgcca cc atg ggg gcc cca gcc gcc tcg ccg gtg ccc ctg ctc          48
              Met Gly Ala Pro Ala Ala Ser Pro Val Pro Leu Leu
                1               5                   10 ctg ctc ctc gcc tgc tcc tgg gcg ccc ggc ggg gcc aat ctt tcc cag       96
Leu Leu Leu Ala Cys Ser Trp Ala Pro Gly Gly Ala Asn Leu Ser Gln
            15                  20                  25 gac gat agc cag ccc tgg aca tct gat gaa aca gtt gtg gct ggt ggc      144
Asp Asp Ser Gln Pro Trp Thr Ser Asp Glu Thr Val Val Ala Gly Gly
        30                  35                  40 aca gtg gtt ctc aag tgt caa gta aaa gac cat gaa gac tca tct ctg      192
Thr Val Val Leu Lys Cys Gln Val Lys Asp His Glu Asp Ser Ser Leu
45                  50                  55                  60 cag tgg tct aac cct gct cag cag acc cta tac ttc ggg gag aag aga      240
Gln Trp Ser Asn Pro Ala Gln Gln Thr Leu Tyr Phe Gly Glu Lys Arg
                65                  70                  75 gcc ctt cga gat aat cgg att cag ctg gtt agc tct act ccc cat gag      288
Ala Leu Arg Asp Asn Arg Ile Gln Leu Val Ser Ser Thr Pro His Glu
            80                  85                  90 ctc agc atc agc atc agc aat gtg gcg ctg gcc gat gag ggg gag tac      336
Leu Ser Ile Ser Ile Ser Asn Val Ala Leu Ala Asp Glu Gly Glu Tyr
        95                  100                 105 acg tgc tcc atc ttc act atg cct gtg cga acc gcc aag tcc ctt gtc      384
Thr Cys Ser Ile Phe Thr Met Pro Val Arg Thr Ala Lys Ser Leu Val
    110                 115                 120 act gtg ctc gga atc cca cag aaa ccc ata atc act ggt tat aag tca      432
Thr Val Leu Gly Ile Pro Gln Lys Pro Ile Ile Thr Gly Tyr Lys Ser
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| 125 |     |     |     |     | 130 |     |     |     |     | 135 |     |     |     |     | 140 |      |
| tca | ttg | cgg | gaa | aag | gag | aca | gcc | act | cta | aat | tgt | cag | tct | tct | ggg | 480  |
| Ser | Leu | Arg | Glu | Lys | Glu | Thr | Ala | Thr | Leu | Asn | Cys | Gln | Ser | Ser | Gly |      |
|     |     |     |     | 145 |     |     |     |     | 150 |     |     |     |     | 155 |     |      |

```
agc aaa cct gca gcc cag ctc acc tgg agg aaa ggt gac caa gaa ctc      528
Ser Lys Pro Ala Ala Gln Leu Thr Trp Arg Lys Gly Asp Gln Glu Leu
            160                 165                 170 cac ggg gac caa aca cga atc cag gaa gat ccc aac ggg aaa acc ttc      576
His Gly Asp Gln Thr Arg Ile Gln Glu Asp Pro Asn Gly Lys Thr Phe
        175                 180                 185 act gtg agc agc tca gtg tca ttc cag gtt acc cgg gag gat gat gga      624
Thr Val Ser Ser Ser Val Ser Phe Gln Val Thr Arg Glu Asp Asp Gly
    190                 195                 200 gca aac atc gtg tgc tct gtg aac cat gaa tct ctg aag gga gcc gac      672
Ala Asn Ile Val Cys Ser Val Asn His Glu Ser Leu Lys Gly Ala Asp
205                 210                 215                 220 aga tcc act tct cag cgc att gaa gtg tta tac aca cca aca gcc atg      720
Arg Ser Thr Ser Gln Arg Ile Glu Val Leu Tyr Thr Pro Thr Ala Met
                225                 230                 235 att agg cca gaa cct gct cat cct cga gaa ggc cag aag ctg ttg tta      768
Ile Arg Pro Glu Pro Ala His Pro Arg Glu Gly Gln Lys Leu Leu Leu
            240                 245                 250 cat tgt gag ggg cgt ggc aat cca gtc ccc cag cag tac gtg tgg gta      816
His Cys Glu Gly Arg Gly Asn Pro Val Pro Gln Gln Tyr Val Trp Val
        255                 260                 265 aag gaa ggc agt gag cca ccc ctc aag atg acc caa gag agt gct ctc      864
Lys Glu Gly Ser Glu Pro Pro Leu Lys Met Thr Gln Glu Ser Ala Leu
    270                 275                 280 atc ttc ccc ttt ttg aat aag agt gac agt ggc act tat ggc tgt aca      912
Ile Phe Pro Phe Leu Asn Lys Ser Asp Ser Gly Thr Tyr Gly Cys Thr
285                 290                 295                 300 gcc aca agc aac atg ggc agc tat aca gcc tac ttc acc ctc aat gtc      960
Ala Thr Ser Asn Met Gly Ser Tyr Thr Ala Tyr Phe Thr Leu Asn Val
                305                 310                 315 aac gac ccc agt cca gtg ccc tcg tcc tcc agt acc tac cac gcc atc     1008
Asn Asp Pro Ser Pro Val Pro Ser Ser Ser Ser Thr Tyr His Ala Ile
            320                 325                 330 att gga ggg att gtg gct ttc att gtc ttc ctg ctg ctc att ctg ctc     1056
Ile Gly Gly Ile Val Ala Phe Ile Val Phe Leu Leu Leu Ile Leu Leu
        335                 340                 345 att ttc ctt gga cac tat ttg att cgg cac aaa gga acc tac ctg aca     1104
Ile Phe Leu Gly His Tyr Leu Ile Arg His Lys Gly Thr Tyr Leu Thr
    350                 355                 360 cac gaa gcg aag ggc tcc gac gat gct cca gat gcg gat acg gcc atc     1152
His Glu Ala Lys Gly Ser Asp Asp Ala Pro Asp Ala Asp Thr Ala Ile
365                 370                 375                 380 atc aac gca gaa ggc ggg cag tca ggg gat gac aag aag gaa tat         1200
Ile Asn Ala Glu Gly Gly Gln Ser Gly Asp Asp Lys Lys Glu Tyr
                385                 390                 395 ttc atc tagggcacc cacacaactc ctgagcccct aggggcccca tgggactgc        1256
Phe Ile tgggctgtcg cggccgc                                                  1273

<210> SEQ ID NO 4
<211> LENGTH: 398
<212> TYPE: PRT
<213> ORGANISM: Mus musculus

<400> SEQUENCE: 4
```

-continued

```
Met Gly Ala Pro Ala Ser Pro Val Pro Leu Leu Leu Leu Ala
 1               5                  10                  15

Cys Ser Trp Ala Pro Gly Gly Ala Asn Leu Ser Gln Asp Ser Gln
                 20                  25                  30

Pro Trp Thr Ser Asp Glu Thr Val Ala Gly Gly Thr Val Val Leu
             35                  40                  45

Lys Cys Gln Val Lys Asp His Glu Asp Ser Ser Leu Gln Trp Ser Asn
 50                  55                  60

Pro Ala Gln Gln Thr Leu Tyr Phe Gly Glu Lys Arg Ala Leu Arg Asp
 65                  70                  75                  80

Asn Arg Ile Gln Leu Val Ser Ser Thr Pro His Glu Leu Ser Ile Ser
                 85                  90                  95

Ile Ser Asn Val Ala Leu Ala Asp Glu Gly Glu Tyr Thr Cys Ser Ile
                100                 105                 110

Phe Thr Met Pro Val Arg Thr Ala Lys Ser Leu Val Thr Val Leu Gly
            115                 120                 125

Ile Pro Gln Lys Pro Ile Ile Thr Gly Tyr Lys Ser Ser Leu Arg Glu
130                 135                 140

Lys Glu Thr Ala Thr Leu Asn Cys Gln Ser Ser Gly Ser Lys Pro Ala
145                 150                 155                 160

Ala Gln Leu Thr Trp Arg Lys Gly Asp Gln Glu Leu His Gly Asp Gln
                165                 170                 175

Thr Arg Ile Gln Glu Asp Pro Asn Gly Lys Thr Phe Thr Val Ser Ser
            180                 185                 190

Ser Val Ser Phe Gln Val Thr Arg Glu Asp Asp Gly Ala Asn Ile Val
        195                 200                 205

Cys Ser Val Asn His Glu Ser Leu Lys Gly Ala Asp Arg Ser Thr Ser
210                 215                 220

Gln Arg Ile Glu Val Leu Tyr Thr Pro Thr Ala Met Ile Arg Pro Glu
225                 230                 235                 240

Pro Ala His Pro Arg Glu Gly Gln Lys Leu Leu Leu His Cys Glu Gly
                245                 250                 255

Arg Gly Asn Pro Val Pro Gln Gln Tyr Val Trp Val Lys Glu Gly Ser
            260                 265                 270

Glu Pro Pro Leu Lys Met Thr Gln Glu Ser Ala Leu Ile Phe Pro Phe
        275                 280                 285

Leu Asn Lys Ser Asp Ser Gly Thr Tyr Gly Cys Thr Ala Thr Ser Asn
290                 295                 300

Met Gly Ser Tyr Thr Ala Tyr Phe Thr Leu Asn Val Asn Asp Pro Ser
305                 310                 315                 320

Pro Val Pro Ser Ser Ser Thr Tyr His Ala Ile Ile Gly Gly Ile
                325                 330                 335

Val Ala Phe Ile Val Phe Leu Leu Leu Ile Leu Leu Ile Phe Leu Gly
            340                 345                 350

His Tyr Leu Ile Arg His Lys Gly Thr Tyr Leu Thr His Glu Ala Lys
        355                 360                 365

Gly Ser Asp Asp Ala Pro Asp Ala Asp Thr Ala Ile Ile Asn Ala Glu
370                 375                 380

Gly Gly Gln Ser Gly Gly Asp Asp Lys Lys Glu Tyr Phe Ile
385                 390                 395
```

<210> SEQ ID NO 5
<211> LENGTH: 1718
<212> TYPE: DNA

-continued

```
<213> ORGANISM: Homo sapien
<220> FEATURE:
<221> NAME/KEY: CDS
<222> LOCATION: 157..1350

<400> SEQUENCE: 5
```

| | | |
|---|---|---|
| aagcttggca cgaggcggtc cccacctcgg ccccgggctc cgaagcggct cggggggcgcc | | 60 |
| ctttcggtca acatcgtagt ccaccccctc cccatcccca gccccgggg attcaggctc | | 120 |
| gccagcgccc agccagggag ccggccggga agcgcg atg ggg gcc cca gcc gcc<br>                                                        Met Gly Ala Pro Ala Ala<br>                                                       1               5 | | 174 |
| tcg ctc ctg ctc ctg ctc ctg ttc gcc tgc tgc tgg gcg ccc ggc<br>Ser Leu Leu Leu Leu Leu Leu Leu Phe Ala Cys Cys Trp Ala Pro Gly<br>                10                        15                      20 | | 222 |
| ggg gcc aac ctc tcc cag gac gac agc cag ccc tgg aca tct gat gaa<br>Gly Ala Asn Leu Ser Gln Asp Asp Ser Gln Pro Trp Thr Ser Asp Glu<br>      25                      30                      35 | | 270 |
| aca gtg gtg gct ggt ggc acc gtg gtg ctc aag tgc caa gtg aaa gat<br>Thr Val Val Ala Gly Gly Thr Val Val Leu Lys Cys Gln Val Lys Asp<br>40                      45                      50 | | 318 |
| cac gag gac tca tcc ctg caa tgg tct aac cct gct cag cag act ctc<br>His Glu Asp Ser Ser Leu Gln Trp Ser Asn Pro Ala Gln Gln Thr Leu<br>55                      60                      65                      70 | | 366 |
| tac ttt ggg gag aag aga gcc ctt cga gat aat cga att cag ctg gtt<br>Tyr Phe Gly Glu Lys Arg Ala Leu Arg Asp Asn Arg Ile Gln Leu Val<br>                75                        80                      85 | | 414 |
| acc tct acg ccc cac gag ctc agc atc agc atc agc aat gtg gcc ctg<br>Thr Ser Thr Pro His Glu Leu Ser Ile Ser Ile Ser Asn Val Ala Leu<br>                        90                      95                   100 | | 462 |
| gca gac gag ggc gag tac acc tgc tca atc ttc act atg cct gtg cga<br>Ala Asp Glu Gly Glu Tyr Thr Cys Ser Ile Phe Thr Met Pro Val Arg<br>               105                      110                    115 | | 510 |
| act gcc aag tcc ctc gtc act gtg cta gga att cca cag aag ccc atc<br>Thr Ala Lys Ser Leu Val Thr Val Leu Gly Ile Pro Gln Lys Pro Ile<br>120                     125                     130 | | 558 |
| atc act ggt tat aaa tct tca tta cgg gaa aaa gac aca gcc acc cta<br>Ile Thr Gly Tyr Lys Ser Ser Leu Arg Glu Lys Asp Thr Ala Thr Leu<br>135                    140                    145                   150 | | 606 |
| aac tgt cag tct tct ggg agc aag cct gca gcc cgg ctc acc tgg aga<br>Asn Cys Gln Ser Ser Gly Ser Lys Pro Ala Ala Arg Leu Thr Trp Arg<br>                 155                      160                    165 | | 654 |
| aag ggt gac caa gaa ctc cac gga gaa cca acc cgc ata cag gaa gat<br>Lys Gly Asp Gln Glu Leu His Gly Glu Pro Thr Arg Ile Gln Glu Asp<br>170                     175                    180 | | 702 |
| ccc aat ggt aaa acc ttc act gtc agc agc tcg gtg aca ttc cag gtt<br>Pro Asn Gly Lys Thr Phe Thr Val Ser Ser Ser Val Thr Phe Gln Val<br>185                    190                    195 | | 750 |
| acc cgg gag gat gat ggg gcg agc atc gtg tgc tct gtg aac cat gaa<br>Thr Arg Glu Asp Asp Gly Ala Ser Ile Val Cys Ser Val Asn His Glu<br>200                     205                    210 | | 798 |
| tct cta aag gga gct gac aga tcc acc tct caa gc att gaa gtt tta<br>Ser Leu Lys Gly Ala Asp Arg Ser Thr Ser Gln Arg Ile Glu Val Leu<br>215                    220                    225                   230 | | 846 |
| tac aca cca act gcg atg att agg cca gac cct ccc cat cct cgt gag<br>Tyr Thr Pro Thr Ala Met Ile Arg Pro Asp Pro Pro His Pro Arg Glu<br>                        235                      240                    245 | | 894 |
| ggc cag aag ctg ttg cta cac tgt gag ggt cgc ggc aat cca gtc ccc<br>Gly Gln Lys Leu Leu Leu His Cys Glu Gly Arg Gly Asn Pro Val Pro<br>250                     255                    260 | | 942 |

```
cag cag tac cta tgg gag aag gag ggc agt gtg cca ccc ctg aag atg      990
Gln Gln Tyr Leu Trp Glu Lys Glu Gly Ser Val Pro Pro Leu Lys Met
            265                 270                 275 acc cag gag agt gcc ctg atc ttc cct ttc ctc aac aag agt gac agt     1038
Thr Gln Glu Ser Ala Leu Ile Phe Pro Phe Leu Asn Lys Ser Asp Ser
    280                 285                 290 ggc acc tac ggc tgc aca gcc acc agc aac atg ggc agc tac aag gcc     1086
Gly Thr Tyr Gly Cys Thr Ala Thr Ser Asn Met Gly Ser Tyr Lys Ala
295                 300                 305                 310 tac tac acc ctc aat gtt aat gac ccc agt ccg gtg ccc tcc tcc tcc     1134
Tyr Tyr Thr Leu Asn Val Asn Asp Pro Ser Pro Val Pro Ser Ser Ser
                315                 320                 325 agc acc tac cac gcc atc atc ggt ggg atc gtg gct ttc att gtc ttc     1182
Ser Thr Tyr His Ala Ile Ile Gly Gly Ile Val Ala Phe Ile Val Phe
            330                 335                 340 ctg ctg ctc atc atg ctc atc ttc ctt ggc cac tac ttg atc cgg cac     1230
Leu Leu Leu Ile Met Leu Ile Phe Leu Gly His Tyr Leu Ile Arg His
            345                 350                 355 aaa gga acc tac ctg aca cat gag gca aaa ggc tcc gat gat gct cca     1278
Lys Gly Thr Tyr Leu Thr His Glu Ala Lys Gly Ser Asp Asp Ala Pro
360                 365                 370 gac gcg gac acg gcc atc atc aat gca gaa ggc ggg cag tca gga ggg     1326
Asp Ala Asp Thr Ala Ile Ile Asn Ala Glu Gly Gly Gln Ser Gly Gly
375                 380                 385                 390 gac gac aag aag gaa tat ttc atc tagaggcgcc tgcccacttc ctgcgccccc    1380
Asp Asp Lys Lys Glu Tyr Phe Ile
                395 cagggggccct gtggggactg ctggggccgt caccaacccg gacttgtaca gagcaaccgc  1440
agggccgccc ctcccgcttg ctccccagcc cacccacccc cctgtacaga atgtctgctt  1500
tgggtgcggt tttgtactcg gtttggaatg ggagggagg agggcggggg gaggggaggg   1560
ttgccctcag ccctttccgt ggcttctctg catttgggtt attattattt ttgtaacaat  1620
cccaaatcaa atctgtctcc aggctggaga ggcaggagcc ctggggtgag aaaagcaaaa  1680
aacaaacaaa aaaaaaaaaa aaaaattcct gcggccgc                          1718

<210> SEQ ID NO 6
<211> LENGTH: 398
<212> TYPE: PRT
<213> ORGANISM: Homo sapien

<400> SEQUENCE: 6

Met Gly Ala Pro Ala Ala Ser Leu Leu Leu Leu Leu Leu Leu Phe Ala
 1               5                  10                  15

Cys Cys Trp Ala Pro Gly Gly Ala Asn Leu Ser Gln Asp Asp Ser Gln
                20                  25                  30

Pro Trp Thr Ser Asp Glu Thr Val Val Ala Gly Gly Thr Val Val Leu
            35                  40                  45

Lys Cys Gln Val Lys Asp His Glu Asp Ser Ser Leu Gln Trp Ser Asn
50                  55                  60

Pro Ala Gln Gln Thr Leu Tyr Phe Gly Glu Lys Arg Ala Leu Arg Asp
65                  70                  75                  80

Asn Arg Ile Gln Leu Val Thr Ser Thr Pro His Glu Leu Ser Ile Ser
                85                  90                  95

Ile Ser Asn Val Ala Leu Ala Asp Glu Gly Glu Tyr Thr Cys Ser Ile
            100                 105                 110

Phe Thr Met Pro Val Arg Thr Ala Lys Ser Leu Val Thr Val Leu Gly
        115                 120                 125
```

-continued

```
Ile Pro Gln Lys Pro Ile Thr Gly Tyr Lys Ser Ser Leu Arg Glu
    130                 135                 140
Lys Asp Thr Ala Thr Leu Asn Cys Gln Ser Ser Gly Ser Lys Pro Ala
145                 150                 155                 160
Ala Arg Leu Thr Trp Arg Lys Gly Asp Gln Glu Leu His Gly Glu Pro
                165                 170                 175
Thr Arg Ile Gln Glu Asp Pro Asn Gly Lys Thr Phe Thr Val Ser Ser
            180                 185                 190
Ser Val Thr Phe Gln Val Thr Arg Glu Asp Asp Gly Ala Ser Ile Val
        195                 200                 205
Cys Ser Val Asn His Glu Ser Leu Lys Gly Ala Asp Arg Ser Thr Ser
    210                 215                 220
Gln Arg Ile Glu Val Leu Tyr Thr Pro Thr Ala Met Ile Arg Pro Asp
225                 230                 235                 240
Pro Pro His Pro Arg Glu Gly Gln Lys Leu Leu Leu His Cys Glu Gly
                245                 250                 255
Arg Gly Asn Pro Val Pro Gln Gln Tyr Leu Trp Glu Lys Glu Gly Ser
            260                 265                 270
Val Pro Pro Leu Lys Met Thr Gln Glu Ser Ala Leu Ile Phe Pro Phe
        275                 280                 285
Leu Asn Lys Ser Asp Ser Gly Thr Tyr Gly Cys Thr Ala Thr Ser Asn
    290                 295                 300
Met Gly Ser Tyr Lys Ala Tyr Tyr Thr Leu Asn Val Asn Asp Pro Ser
305                 310                 315                 320
Pro Val Pro Ser Ser Ser Thr Tyr His Ala Ile Ile Gly Gly Ile
                325                 330                 335
Val Ala Phe Ile Val Phe Leu Leu Leu Ile Met Leu Ile Phe Leu Gly
            340                 345                 350
His Tyr Leu Ile Arg His Lys Gly Thr Tyr Leu Thr His Glu Ala Lys
        355                 360                 365
Gly Ser Asp Asp Ala Pro Asp Ala Asp Thr Ala Ile Ile Asn Ala Glu
    370                 375                 380
Gly Gly Gln Ser Gly Gly Asp Asp Lys Lys Glu Tyr Phe Ile
385                 390                 395
```

```
<210> SEQ ID NO 7
<211> LENGTH: 16
<212> TYPE: DNA
<213> ORGANISM: Artifical Sequence
<220> FEATURE:
<223> OTHER INFORMATION: Oligonucleotide primer from Homo sapiens

<400> SEQUENCE: 7
agggcgagta cacctg                                                   16

<210> SEQ ID NO 8
<211> LENGTH: 17
<212> TYPE: DNA
<213> ORGANISM: Artifical Sequence
<220> FEATURE:
<223> OTHER INFORMATION: Oligonucleotide primer from Homo sapien

<400> SEQUENCE: 8
gtggatctgt cagctcc                                                  17

<210> SEQ ID NO 9
<211> LENGTH: 16
```

```
<212> TYPE: DNA
<213> ORGANISM: Artifical Sequence
<220> FEATURE:
<223> OTHER INFORMATION: Oligonucleotide from Homo sapien

<400> SEQUENCE: 9
tcgacatgga tccaca                                                       16

<210> SEQ ID NO 10
<211> LENGTH: 16
<212> TYPE: DNA
<213> ORGANISM: Artifical Sequence
<220> FEATURE:
<223> OTHER INFORMATION: Oligonucleotide from Homo sapien

<400> SEQUENCE: 10
agcttgtgga tccatg                                                       16

<210> SEQ ID NO 11
<211> LENGTH: 35
<212> TYPE: DNA
<213> ORGANISM: Homo sapien

<400> SEQUENCE: 11
atatggatcc gtcgacggat tcaggctcgc cagcg                                  35

<210> SEQ ID NO 12
<211> LENGTH: 36
<212> TYPE: DNA
<213> ORGANISM: Artifical Sequence
<220> FEATURE:
<223> OTHER INFORMATION: Oligonucleotide primer from Mus musculus

<400> SEQUENCE: 12
atatggatcc agatctgtgg taggtgctgg aggagg                                 36

<210> SEQ ID NO 13
<211> LENGTH: 30
<212> TYPE: DNA
<213> ORGANISM: Artifical Sequence
<220> FEATURE:
<223> OTHER INFORMATION: Oligonucleotide primer from Mus musculus

<400> SEQUENCE: 13
atatactagt cccggcgggg ccaacctctc                                        30

<210> SEQ ID NO 14
<211> LENGTH: 21
<212> TYPE: DNA
<213> ORGANISM: Artifical Sequence
<220> FEATURE:
<223> OTHER INFORMATION: Oligonucleotide primer from Homo sapien

<400> SEQUENCE: 14
cctgctgttc gcctgctgct g                                                 21

<210> SEQ ID NO 15
<211> LENGTH: 20
<212> TYPE: DNA
<213> ORGANISM: Artifical Sequence
<220> FEATURE:
<223> OTHER INFORMATION: Oligonucleotide from Homo sapien

<400> SEQUENCE: 15
ctgctgagca gggttagacc                                                   20
```

```
<210> SEQ ID NO 16
<211> LENGTH: 59
<212> TYPE: DNA
<213> ORGANISM: Artifical Sequence
<220> FEATURE:
<223> OTHER INFORMATION: Oligonucleotide primer from Homo sapien

<400> SEQUENCE: 16
atatgtcgac gccaccatgg gggccccagc cgcctcgccg gtgcccctgc tcctgctcc      59

<210> SEQ ID NO 17
<211> LENGTH: 24
<212> TYPE: DNA
<213> ORGANISM: Artifical Sequence
<220> FEATURE:
<223> OTHER INFORMATION: Oligonucleotide primer from Mus musculus

<400> SEQUENCE: 17
atatgtcgac gccaccatgg gggc                                            24

<210> SEQ ID NO 18
<211> LENGTH: 30
<212> TYPE: DNA
<213> ORGANISM: Artifical Sequence
<220> FEATURE:
<223> OTHER INFORMATION: Oligonucleotide primer from Mus musculus

<400> SEQUENCE: 18
atatgcggcc gcgacagccc agcagtcccc                                      30

<210> SEQ ID NO 19
<211> LENGTH: 1598
<212> TYPE: DNA
<213> ORGANISM: Homo sapien
<220> FEATURE:
<221> NAME/KEY: CDS
<222> LOCATION: 16..1341

<400> SEQUENCE: 19
gcggccgcgc ccgac atg gcg agt gta gtg ctg ccg agc gga tcc cag tgt     51
                Met Ala Ser Val Val Leu Pro Ser Gly Ser Gln Cys
                 1               5                  10 gcg gcg gca gcg gcg gcg gcg gcg cct ccc ggg ctc cgg ctc cgg ctt      99
Ala Ala Ala Ala Ala Ala Ala Ala Pro Pro Gly Leu Arg Leu Arg Leu
         15                  20                  25 ctg ctg ttg ctc ttc tcc gcc gcg gca ctg atc ccc aca ggt gat ggg     147
Leu Leu Leu Leu Phe Ser Ala Ala Ala Leu Ile Pro Thr Gly Asp Gly
 30                  35                  40 cag aat ctg ttt acg aaa gac gtg aca gtg atc gag gga gag gtt gcg     195
Gln Asn Leu Phe Thr Lys Asp Val Thr Val Ile Glu Gly Glu Val Ala
 45                  50                  55                  60 acc atc agt tgc caa gtc aat aag agt gac gac tct gtg att cag cta     243
Thr Ile Ser Cys Gln Val Asn Lys Ser Asp Asp Ser Val Ile Gln Leu
             65                  70                  75 ctg aat ccc aac agg cag acc att tat ttc agg gac ttc agg cct ttg     291
Leu Asn Pro Asn Arg Gln Thr Ile Tyr Phe Arg Asp Phe Arg Pro Leu
         80                  85                  90 aag gac agc agg ttt cag ttg ctg aat ttt tct agc agt gaa ctc aaa     339
Lys Asp Ser Arg Phe Gln Leu Leu Asn Phe Ser Ser Ser Glu Leu Lys
     95                 100                 105 gta tca ttg aca aac gtc tca att tct gat gaa gga aga tac ttt tgc     387
Val Ser Leu Thr Asn Val Ser Ile Ser Asp Glu Gly Arg Tyr Phe Cys
110                 115                 120
```

```
cag ctc tat acc gat ccc cca cag gaa agt tac acc acc atc aca gtc      435
Gln Leu Tyr Thr Asp Pro Pro Gln Glu Ser Tyr Thr Thr Ile Thr Val
125                 130                 135                 140 ctg gtc cca cca cgt aat ctg atg atc gat atc cag aaa gac act gcg      483
Leu Val Pro Pro Arg Asn Leu Met Ile Asp Ile Gln Lys Asp Thr Ala
            145                 150                 155 gtg gaa ggt gag gag att gaa gtc aac tgc act gct atg gcc agc aag      531
Val Glu Gly Glu Glu Ile Glu Val Asn Cys Thr Ala Met Ala Ser Lys
                160                 165                 170 cca gcc acg act atc agg tgg ttc aaa ggg aac aca gag cta aaa ggc      579
Pro Ala Thr Thr Ile Arg Trp Phe Lys Gly Asn Thr Glu Leu Lys Gly
            175                 180                 185 aaa tcg gag gtg gaa gag tgg tca gac atg tac act gtg acc agt cag      627
Lys Ser Glu Val Glu Glu Trp Ser Asp Met Tyr Thr Val Thr Ser Gln
    190                 195                 200 ctg atg ctg aag gtg cac aag gag gac gat ggg gtc cca gtg atc tgc      675
Leu Met Leu Lys Val His Lys Glu Asp Asp Gly Val Pro Val Ile Cys
205                 210                 215                 220 cag gtg gag cac cct gcg gtc act gga aac ctg cag acc cag cgg tat      723
Gln Val Glu His Pro Ala Val Thr Gly Asn Leu Gln Thr Gln Arg Tyr
                225                 230                 235 cta gaa gta cag tat aag cct caa gtg cac att cag atg act tat cct      771
Leu Glu Val Gln Tyr Lys Pro Gln Val His Ile Gln Met Thr Tyr Pro
            240                 245                 250 cta caa ggc tta acc cgg gaa ggg gac gcg ctt gag tta aca tgt gaa      819
Leu Gln Gly Leu Thr Arg Glu Gly Asp Ala Leu Glu Leu Thr Cys Glu
            255                 260                 265 gcc atc ggg aag ccc cag cct gtg atg gta act tgg gtg aga gtc gat      867
Ala Ile Gly Lys Pro Gln Pro Val Met Val Thr Trp Val Arg Val Asp
270                 275                 280 gat gaa atg cct caa cac gcc gta ctg tct ggg ccc aac ctg ttc atc      915
Asp Glu Met Pro Gln His Ala Val Leu Ser Gly Pro Asn Leu Phe Ile
285                 290                 295                 300 aat aac cta aac aaa aca gat aat ggt aca tac cgc tgt gaa gct tca      963
Asn Asn Leu Asn Lys Thr Asp Asn Gly Thr Tyr Arg Cys Glu Ala Ser
                305                 310                 315 aac ata gtg ggg aaa gct cac tcg gat tat atg ctg tat gta tac gat     1011
Asn Ile Val Gly Lys Ala His Ser Asp Tyr Met Leu Tyr Val Tyr Asp
            320                 325                 330 ccc ccc aca act atc cct cct ccc aca aca acc acc acc acc acc acc     1059
Pro Pro Thr Thr Ile Pro Pro Pro Thr Thr Thr Thr Thr Thr Thr Thr
            335                 340                 345 acc acc acc acc acc atc ctt acc atc atc aca gat tcc cga gca ggt     1107
Thr Thr Thr Thr Thr Ile Leu Thr Ile Ile Thr Asp Ser Arg Ala Gly
350                 355                 360 gaa gaa ggc tcg atc agg gca gtg gat cat gcc gtg atc ggt ggc gtc     1155
Glu Glu Gly Ser Ile Arg Ala Val Asp His Ala Val Ile Gly Gly Val
365                 370                 375                 380 gtg gcg gtg gtg gtg ttc gcc atg ctg tgc ttg ctc atc att ctg ggg     1203
Val Ala Val Val Val Phe Ala Met Leu Cys Leu Leu Ile Ile Leu Gly
                385                 390                 395 cgc tat ttt gcc aga cat aaa ggt aca tac ttc act cat gaa gcc aaa     1251
Arg Tyr Phe Ala Arg His Lys Gly Thr Tyr Phe Thr His Glu Ala Lys
            400                 405                 410 gga gcc gat gac gca gca gac gca gac aca gct ata atc aat gca gaa     1299
Gly Ala Asp Asp Ala Ala Asp Ala Asp Thr Ala Ile Ile Asn Ala Glu
            415                 420                 425 gga gga cag aac aac tcc gaa gaa aag aaa gag tac ttc atc                 1341
Gly Gly Gln Asn Asn Ser Glu Glu Lys Lys Glu Tyr Phe Ile
430                 435                 440
```

```
tagatcagcc tttttgtttc aatgaggtgt ccaactggcc ctatttagat gataaagaga   1401
cagtgatatt ggaacttgcg agaaattcgt gtgttttttt atgaatgggt ggaaaggtgt   1461
gagactggga aggcttggga tttgctgtgt aaaaaaaaaa aaaaaatgtt ctttggaaag   1521
aaaaaagcgg ccgctttctt attctatttc aacattcagc ttaatcataa tcctaaaatc   1581
atacatgcta tttccat                                                  1598

<210> SEQ ID NO 20
<211> LENGTH: 442
<212> TYPE: PRT
<213> ORGANISM: Homo sapien

<400> SEQUENCE: 20
```

Met Ala Ser Val Val Leu Pro Ser Gly Ser Gln Cys Ala Ala Ala
 1               5                  10                  15

Ala Ala Ala Pro Pro Gly Leu Arg Leu Arg Leu Leu Leu Leu Leu
            20                  25                  30

Phe Ser Ala Ala Ala Leu Ile Pro Thr Gly Asp Gly Gln Asn Leu Phe
            35                  40                  45

Thr Lys Asp Val Thr Val Ile Glu Gly Glu Val Ala Thr Ile Ser Cys
 50                  55                  60

Gln Val Asn Lys Ser Asp Asp Ser Val Ile Gln Leu Leu Asn Pro Asn
 65                  70                  75                  80

Arg Gln Thr Ile Tyr Phe Arg Asp Phe Arg Pro Leu Lys Asp Ser Arg
                85                  90                  95

Phe Gln Leu Leu Asn Phe Ser Ser Ser Glu Leu Lys Val Ser Leu Thr
            100                 105                 110

Asn Val Ser Ile Ser Asp Glu Gly Arg Tyr Phe Cys Gln Leu Tyr Thr
            115                 120                 125

Asp Pro Pro Gln Glu Ser Tyr Thr Thr Ile Thr Val Leu Val Pro Pro
        130                 135                 140

Arg Asn Leu Met Ile Asp Ile Gln Lys Asp Thr Ala Val Glu Gly Glu
145                 150                 155                 160

Glu Ile Glu Val Asn Cys Thr Ala Met Ala Ser Lys Pro Ala Thr Thr
                165                 170                 175

Ile Arg Trp Phe Lys Gly Asn Thr Glu Leu Lys Gly Lys Ser Glu Val
            180                 185                 190

Glu Glu Trp Ser Asp Met Tyr Thr Val Thr Ser Gln Leu Met Leu Lys
        195                 200                 205

Val His Lys Glu Asp Asp Gly Val Pro Val Ile Cys Gln Val Glu His
    210                 215                 220

Pro Ala Val Thr Gly Asn Leu Gln Thr Gln Arg Tyr Leu Glu Val Gln
225                 230                 235                 240

Tyr Lys Pro Gln Val His Ile Gln Met Thr Tyr Pro Leu Gln Gly Leu
                245                 250                 255

Thr Arg Glu Gly Asp Ala Leu Glu Leu Thr Cys Glu Ala Ile Gly Lys
            260                 265                 270

Pro Gln Pro Val Met Val Thr Trp Val Arg Val Asp Asp Glu Met Pro
        275                 280                 285

Gln His Ala Val Leu Ser Gly Pro Asn Leu Phe Ile Asn Asn Leu Asn
    290                 295                 300

Lys Thr Asp Asn Gly Thr Tyr Arg Cys Glu Ala Ser Asn Ile Val Gly
305                 310                 315                 320

```
Lys Ala His Ser Asp Tyr Met Leu Tyr Val Asp Pro Pro Thr Thr
            325                 330                 335

Ile Pro Pro Thr Thr Thr Thr Thr Thr Thr Thr Thr Thr Thr Thr
            340                 345                 350

Thr Ile Leu Thr Ile Ile Thr Asp Ser Arg Ala Gly Glu Glu Gly Ser
            355                 360                 365

Ile Arg Ala Val Asp His Ala Val Ile Gly Gly Val Ala Val Val
370                 375                 380

Val Phe Ala Met Leu Cys Leu Leu Ile Ile Leu Gly Arg Tyr Phe Ala
385                 390                 395                 400

Arg His Lys Gly Thr Tyr Phe Thr His Glu Ala Lys Gly Ala Asp Asp
            405                 410                 415

Ala Ala Asp Ala Asp Thr Ala Ile Ile Asn Ala Glu Gly Gly Gln Asn
            420                 425                 430

Asn Ser Glu Glu Lys Lys Glu Tyr Phe Ile
            435                 440
```

<210> SEQ ID NO 21
<211> LENGTH: 1935
<212> TYPE: DNA
<213> ORGANISM: Mus musculus
<220> FEATURE:
<221> NAME/KEY: CDS
<222> LOCATION: 2..1272

<400> SEQUENCE: 21

```
g gcg gcg cct cca ggg ctc cgg ctc cgg ctc ctg ctg ttg ctc ctt         46
  Ala Ala Pro Pro Gly Leu Arg Leu Arg Leu Leu Leu Leu Leu Leu
  1               5                   10                  15 tcg gcc gcg gca ctg atc ccc aca ggt gat gga cag aat ctg ttt act       94
Ser Ala Ala Ala Leu Ile Pro Thr Gly Asp Gly Gln Asn Leu Phe Thr
                20                  25                  30 aaa gac gtg aca gtg att gaa gga gaa gtg gca acc atc agc tgc cag      142
Lys Asp Val Thr Val Ile Glu Gly Glu Val Ala Thr Ile Ser Cys Gln
            35                  40                  45 gtc aat aag agt gac gac tca gtg atc cag ctc ctg aac ccc aac agg      190
Val Asn Lys Ser Asp Asp Ser Val Ile Gln Leu Leu Asn Pro Asn Arg
        50                  55                  60 cag acc att tac ttc agg gac ttc agg cct ttg aag gac agc agg ttt      238
Gln Thr Ile Tyr Phe Arg Asp Phe Arg Pro Leu Lys Asp Ser Arg Phe
65                  70                  75 cag ctg ctg aat ttt tct agc agt gaa ctc aaa gtg tca ctg acg aat      286
Gln Leu Leu Asn Phe Ser Ser Ser Glu Leu Lys Val Ser Leu Thr Asn
80                  85                  90                  95 gtc tca atc tcg gat gaa ggg aga tac ttc tgc cag ctc tac acg gac      334
Val Ser Ile Ser Asp Glu Gly Arg Tyr Phe Cys Gln Leu Tyr Thr Asp
                100                 105                 110 ccc cca cag gag agt tac acc acc atc aca gtc ctg gtt cct cca cgt      382
Pro Pro Gln Glu Ser Tyr Thr Thr Ile Thr Val Leu Val Pro Pro Arg
            115                 120                 125 aac ttg atg atc gat atc cag aaa gac acg gca gtt gaa ggg gag gag      430
Asn Leu Met Ile Asp Ile Gln Lys Asp Thr Ala Val Glu Gly Glu Glu
        130                 135                 140 att gaa gtc aac tgt act gcc atg gcc agc aag cca gcg acg acc atc      478
Ile Glu Val Asn Cys Thr Ala Met Ala Ser Lys Pro Ala Thr Thr Ile
145                 150                 155 agg tgg ttc aaa ggg aac aag gaa ctc aaa ggc aaa tca gag gtg gag      526
Arg Trp Phe Lys Gly Asn Lys Glu Leu Lys Gly Lys Ser Glu Val Glu
160                 165                 170                 175
```

-continued

| | |
|---|---|
| gag tgg tcg gac atg tac act gtg acc agt cag ctg atg ctg aag gtg<br>Glu Trp Ser Asp Met Tyr Thr Val Thr Ser Gln Leu Met Leu Lys Val<br>                                 180                         185                            190 | 574 |
| cac aag gag gac gac ggg gtc ccg gtg atc tgc cag gtg gag cac cct<br>His Lys Glu Asp Asp Gly Val Pro Val Ile Cys Gln Val Glu His Pro<br>               195                          200                         205 | 622 |
| gcg gtc act gga aac ctg cag acc cag cgc tat cta gaa gtg cag tat<br>Ala Val Thr Gly Asn Leu Gln Thr Gln Arg Tyr Leu Glu Val Gln Tyr<br>210                   215                       220 | 670 |
| aaa ccg caa gtg cat atc cag atg act tac cct ctg caa ggc cta acc<br>Lys Pro Gln Val His Ile Gln Met Thr Tyr Pro Leu Gln Gly Leu Thr<br>         225                        230                       235 | 718 |
| cgg gaa ggg gat gca ttt gag tta acg tgt gaa gcc atc ggg aag ccc<br>Arg Glu Gly Asp Ala Phe Glu Leu Thr Cys Glu Ala Ile Gly Lys Pro<br>240                   245                       250                     255 | 766 |
| cag cct gtg atg gta act tgg gtg aga gtc gat gat gaa atg cct caa<br>Gln Pro Val Met Val Thr Trp Val Arg Val Asp Asp Glu Met Pro Gln<br>                  260                        265                     270 | 814 |
| cat gcc gta ctg tct ggg cca aac ctg ttc atc aat aac cta aac aaa<br>His Ala Val Leu Ser Gly Pro Asn Leu Phe Ile Asn Asn Leu Asn Lys<br>             275                      280                       285 | 862 |
| aca gat aac ggt act tac cgc tgt gag gct tcc aac ata gtg gga aag<br>Thr Asp Asn Gly Thr Tyr Arg Cys Glu Ala Ser Asn Ile Val Gly Lys<br>290                   295                       300 | 910 |
| gct cat tcg gac tat atg ctg tat gta tac gat ccc ccc aca act atc<br>Ala His Ser Asp Tyr Met Leu Tyr Val Tyr Asp Pro Pro Thr Thr Ile<br>         305                        310                       315 | 958 |
| cct cct ccc aca aca acc acc acc act acc acc acc acc acc acc acc<br>Pro Pro Pro Thr Thr Thr Thr Thr Thr Thr Thr Thr Thr Thr Thr Thr<br>320                   325                       330                   335 | 1006 |
| atc ctt acc atc atc aca gat tct cga gca ggt gaa gag ggg acc att<br>Ile Leu Thr Ile Ile Thr Asp Ser Arg Ala Gly Glu Glu Gly Thr Ile<br>                  340                       345                   350 | 1054 |
| ggg gca gtg gac cac gca gtg att ggt ggc gtc gta gcc gtg gtg gtg<br>Gly Ala Val Asp His Ala Val Ile Gly Gly Val Val Ala Val Val Val<br>             355                      360                       365 | 1102 |
| ttt gcc atg cta tgc ttg ctc atc att ctg ggc cgc tat ttt gcc aga<br>Phe Ala Met Leu Cys Leu Leu Ile Ile Leu Gly Arg Tyr Phe Ala Arg<br>370                   375                       380 | 1150 |
| cat aaa ggt aca tac ttc act cat gaa gcc aaa gga gcc gat gac gca<br>His Lys Gly Thr Tyr Phe Thr His Glu Ala Lys Gly Ala Asp Asp Ala<br>         385                        390                       395 | 1198 |
| gca gac gca gac aca gct ata atc aat gca gaa gga gga cag aac aac<br>Ala Asp Ala Asp Thr Ala Ile Ile Asn Ala Glu Gly Gly Gln Asn Asn<br>400                   405                       410                   415 | 1246 |
| tcc gaa gaa aag aaa gag tac ttc at ctagatcagc cttttttgttc<br>Ser Glu Glu Lys Lys Glu Tyr Phe<br>                  420 | 1292 |
| caatgaggtg tccaactggc ctgtttagat gataaagaga cagtgatact ggaactttcg | 1352 |
| agaagctcgt gtggtttttt gttttgtttt gtttttttat gagtgggtgg agagatgcga | 1412 |
| gactgggaag gcttgggatt tgcaatgtac aaacaaaaac aaagaatgtt ctttgaaagt | 1472 |
| acactctgct gtttgacacc tcttttaat ctggttttaa tttgctttgg gttttgggtt | 1532 |
| tttttggttt tttgtttttt tcatttatat ttcttcctac caagtcaaac ttgggtactt | 1592 |
| ggatttggtt tcggtagatt gcagaaaatt ctgtgccttg ttttcattc gtttgttgtg | 1652 |
| tttcttccct cttgcccatt tattttccc aaaatcaaat ttgttttttt cccctccca | 1712 |
| aacctcccat tttttggaat tgacctgctg gaattcctaa gactttctcc ctgttgccag | 1772 |

```
tttcttttat ttgtgttaac ggtgactgct ttctgttcca aattcagttt cataaaagga    1832
aaaccagcac aatttagatt tcatagttca gaatttagtg tctccatgat gcatccttct    1892
ctgttgttgt aaagatttgg gtgaagaaaa aaaaaaaaaa aaa                       1935
```

<210> SEQ ID NO 22
<211> LENGTH: 423
<212> TYPE: PRT
<213> ORGANISM: Mus musculus

<400> SEQUENCE: 22

```
Ala Ala Pro Pro Gly Leu Arg Leu Arg Leu Leu Leu Leu Leu Leu Ser
  1               5                  10                  15

Ala Ala Ala Leu Ile Pro Thr Gly Asp Gly Gln Asn Leu Phe Thr Lys
             20                  25                  30

Asp Val Thr Val Ile Glu Gly Glu Val Ala Thr Ile Ser Cys Gln Val
         35                  40                  45

Asn Lys Ser Asp Asp Ser Val Ile Gln Leu Leu Asn Pro Asn Arg Gln
     50                  55                  60

Thr Ile Tyr Phe Arg Asp Phe Arg Pro Leu Lys Asp Ser Arg Phe Gln
 65                  70                  75                  80

Leu Leu Asn Phe Ser Ser Glu Leu Lys Val Ser Leu Thr Asn Val
                 85                  90                  95

Ser Ile Ser Asp Glu Gly Arg Tyr Phe Cys Gln Leu Tyr Thr Asp Pro
            100                 105                 110

Pro Gln Glu Ser Tyr Thr Thr Ile Thr Val Leu Val Pro Pro Arg Asn
        115                 120                 125

Leu Met Ile Asp Ile Gln Lys Asp Thr Ala Val Glu Gly Glu Glu Ile
    130                 135                 140

Glu Val Asn Cys Thr Ala Met Ala Ser Lys Pro Ala Thr Thr Ile Arg
145                 150                 155                 160

Trp Phe Lys Gly Asn Lys Glu Leu Lys Gly Lys Ser Glu Val Glu Glu
                165                 170                 175

Trp Ser Asp Met Tyr Thr Val Thr Ser Gln Leu Met Leu Lys Val His
            180                 185                 190

Lys Glu Asp Asp Gly Val Pro Val Ile Cys Gln Val Glu His Pro Ala
        195                 200                 205

Val Thr Gly Asn Leu Gln Thr Gln Arg Tyr Leu Glu Val Gln Tyr Lys
    210                 215                 220

Pro Gln Val His Ile Gln Met Thr Tyr Pro Leu Gln Gly Leu Thr Arg
225                 230                 235                 240

Glu Gly Asp Ala Phe Glu Leu Thr Cys Glu Ala Ile Gly Lys Pro Gln
                245                 250                 255

Pro Val Met Val Thr Trp Val Arg Val Asp Asp Glu Met Pro Gln His
            260                 265                 270

Ala Val Leu Ser Gly Pro Asn Leu Phe Ile Asn Asn Leu Asn Lys Thr
        275                 280                 285

Asp Asn Gly Thr Tyr Arg Cys Glu Ala Ser Asn Ile Val Gly Lys Ala
    290                 295                 300

His Ser Asp Tyr Met Leu Tyr Val Tyr Asp Pro Pro Thr Thr Ile Pro
305                 310                 315                 320

Pro Pro Thr Thr Thr Thr Thr Thr Thr Thr Thr Thr Thr Thr Thr Ile
                325                 330                 335

Leu Thr Ile Ile Thr Asp Ser Arg Ala Gly Glu Glu Gly Thr Ile Gly
```

-continued

```
                   340                 345                 350
Ala Val Asp His Ala Val Ile Gly Gly Val Val Ala Val Val Val Phe
            355                 360                 365

Ala Met Leu Cys Leu Leu Ile Ile Leu Gly Arg Tyr Phe Ala Arg His
        370                 375                 380

Lys Gly Thr Tyr Phe Thr His Glu Ala Lys Gly Ala Asp Asp Ala Ala
385                 390                 395                 400

Asp Ala Asp Thr Ala Ile Ile Asn Ala Glu Gly Gly Gln Asn Asn Ser
            405                 410                 415

Glu Glu Lys Lys Glu Tyr Phe
            420
```

MOLECULES DESIGNATED B7L-1

CROSS REFERENCE TO RELATED APPLICATIONS

This application is a continuation of pending International Application No. PCT/US99/17906, filed Aug. 5, 1999, which was published under PCT Article 21(2) on Feb. 17, 2000, in English, as WO 00/08057, and which claims the benefit of U.S. Provisional Patent Application Serial No. 60/095,663, filed Aug. 7, 1998, now abandoned. International Application No. PCT/US99/17906 and U.S. Provisional Patent Application Serial No. 60/095,663 are incorporated herein by reference.

FIELD OF THE INVENTION

The present invention relates to a novel polypeptide, designated B7L-1. B7L-1 has weak homology to a number of proteins including B7-1, (CD80) and is a binding protein for LDCAM. The invention includes B7L-1 molecules, DNA encoding B7L-1 molecules, processes for production of recombinant B7L-1 polypeptides, and pharmaceutical compositions containing such B7L-1 polypeptides.

BACKGROUND OF THE INVENTION

B7-1 (CD80) is a T cell costimulatory molecule that is found on the surface of antigen presenting cells (APCs). Originally described as a cell adhesion molecule, it is now known that B7-1 sends important costimulatory signals through its two T cell surface receptors, CD28 and CTLA4 (CD152). B7-1 interacts with CD28 to signal cytokine production, cell proliferation, and the generation of effector and memory T cells. If the signal through CD28 is blocked T cell, anergy or immune deviation can occur, resulting in severely depressed or altered immune response. For example, when B7-1 and (B7-2) interaction with CD28 (and CTLA40 is blocked with a soluble CTLA4Ig, allograft tolerance and resistance to autoimmune diseases have been observed.

B7-1 also interacts with the T cell CTLA4 receptor. Its signaling is complex, but one component provides a negative feedback signal, causing the T cell to attenuate the CD28 signal. In the absence of this signal for a long period of time, rampant T cell proliferation and effector cell activation continues. However, shorter term intervention can be beneficial by leading to a more vigorous immune response. For example, when the interaction of B7-1 (and B7-2) is blocked with antibodies to CTLA4 increased rejection of tumors has been found. When this feedback regulation malfunctions, autoimmune diseases and lymphoproliferation (refs) can result. For example, when the CTLA4 and B7-1 interaction is blocked with a soluble CTLA4Ig, allograft tolerance and resistance to autoimmune diseases have been observed.

In addition to B7-1, other molecules are known to send costimulatory signals to T cells. For example, B7-2 (CD86), which is expressed on different cells and at different stages of APC activation from that of B7-1, also delivers its costimulatory signal to T cells through CD28 and CTLA4. The B7-2 signal can lead to immune responses that are identical to, or different from the immune responses resulting from B7-1 signaling. The nature of the B7-2 signaling depends upon the cellular context and the timing of the costimulation.

Some evidence suggests that additional molecules bind CTLA4. Evidence also exists that other molecules are involved in sending important CD28-independent costimulatory signals to T cells.

Even though they bind to the same cellular receptors, B7-1 and B7-2 are only weakly related at the amino acid level. Both, however, are members of the extended immunoglobulin domain containing superfamily and much of their shared sequence homology is due to the particular residues shared by their common Ig domains, which are characteristic of the Ig-domain subfamily.

Clearly, costimulatory signaling through T cell surface receptors plays an important role in maintaining balance in the immune system. Systems with a predominance of activatory signals, such as the costimulatory signaling between CD28 and B7-1, can lead to autoimmunity and inflammation. Immune systems with a predominance of inhibitory signals, such as the costimulatory signaling between CTLA4 and are less able to challenge infected cells or cancer cells. Isolating new molecules involved in costimulatory signaling is highly desirable for studying the biological signal(s) transduced via the receptor. Additionally, identifying such molecules provides a means of regulating and treating diseased states associated with autoimmunity, inflammation and infection. For example, engaging a molecule that stimulates inhibitory or negative signaling with an agonistic antibody or signaling partner can be used to downregulate a cell function in disease states in which the immune system is overactive and excessive inflammation or immunopathology is present. On the other hand, using an antagonistic antibody specific for a molecule that stimulates negative signaling, or using a soluble form of the molecule to block signaling, can activate the specific immune function in disease states associated with suppressed immune function. Conversely, engaging a molecule that stimulates positive signaling with an agonistic antibody can be used to upregulate the effect of that molecule's signaling.

In view of the evidence that undefined T cell costimulatory molecules exist and further in view of the continuing search for new therapeutics for treating infection, autoimmune diseases, and inflammation, it would be desirable to identify additional T-cell costimulatory molecules. In particular there is a need for additional molecules that alter T cell costimulation during an in vivo immune response.

SUMMARY OF THE INVENTION

The present invention provides mammalian B7L1 polypeptides as isolated or homogeneous proteins. The present invention further includes isolated DNAs encoding B7L1 and expression vectors comprising DNA encoding mammalian B7L1. Within the scope of this invention are host cells that have been transfected or transformed with expression vectors that comprise a DNA encoding B7L1, and processes for producing B7L1 by culturing such host cells under conditions conducive to expression of B7L1. Further within the present invention are pharmaceutical composition comprising soluble forms B7L-1 molecules.

DETAILED DESCRIPTION OF THE INVENTION

Novel proteins, designated B7L-1, and DNA that encodes B7L-1 proteins are provided herein. The B7L-1 polypeptides of the present invention share a weak homology with B7-1 and is are binding proteins for LDCAM, a novel polypeptide, described in copending application Ser. No. 60/095,672 filed Aug. 7, 1998. The human and murine LDCAM nucleotide sequence is disclosed in SEQ ID NO:19 and SEQ ID NO:21, respectively. The amino acid sequences encoded by SEQ ID NO:19 and SEQ ID NO:21 are shown in SEQ ID NO:20 and SEQ ID NO:22, respectively. Mammalian B7L-1 proteins exist as different splice forms, designated long extracellular and short extracellular forms.

Example 1 describes identifying and isolating a full length human clone, designated here-in as long extracellular B7L-1. The nucleotide sequence of human long extracellular B7L-1 DNA, isolated as described in Example 1, is presented in SEQ ID NO:1, and the amino acid sequence encoded thereby is presented in SEQ ID NO:2. The encoded long extracellular human B7L-1 amino acid sequence (SEQ ID NO:2) has a predicted extracellular domain of 364 amino acids (1–364) including a leader sequence of 20 amino acids (1–20); a transmembrane domain of 21 amino acids (365–385) and a cytoplasmic domain of 47 amino acids (386–432).

Example 3 describes isolating a murine B7L-1 DNA with a shorter extracellular region. This DNA is disclosed in SEQ ID NO:3. The amino acid sequence encoded by the nucleotide sequence of SEQ ID NO:3 is disclosed in SEQ ID NO:4. The encoded short extracellular murine B7L-1 amino acid sequence (SEQ ID NO:4) has a predicted extracellular domain of 330 amino acids (1–330), including a leader sequence of 20 amino acids (1–20); a transmembrane domain of 21 amino acids (331–351); and a cytoplasmic domain of 47 amino acids (352–398). The leader sequence of SEQ ID NO:4 includes the first 8 amino acids of the isolated human B7L-1 long molecule.

Example 3 also describes a "short extracellular" form of human B7L-1 DNA that is thought to be an alternatively spliced B7L-1 variant. The nucleotide sequence for the "short extracellular" form is disclosed in SEQ ID NO:5 and the amino acid sequence encoded by the sequence of SEQ ID NO:5 is described in SEQ ID NO:6. The encoded short extracellular human B7L-1 amino acid sequence (SEQ ID NO:6) has a predicted extracellular domain of 330 amino acids including a leader sequence of 20 amino acids; a transmembrane domain of 21 amino acids 331–351; and a cytoplasmic domain of 47 amino acids 352–398. The sequences described in SEQ ID NO:5 and SEQ ID NO:6 were obtained by isolating a clone from human cDNA with primers designed to flank the potential alternative splice between "long" and "short" forms and then comparing a resulting cloned fragment of SEQ ID NO:5 (nucleotides 193–358), the murine short extracellular form described in SEQ ID NO:3 and SEQ ID NO:4 and the human long extracellular form described in SEQ ID NO:1 and SEQ ID NO:2. The comparison confirmed the existence of a human short extracellular form and provided a basis for the sequences of SEQ ID NOS:5 and 6.

The purified mammalian B7L-1 molecules described herein are Type I transmembrane proteins having limited homology to B7-1, poliovirus receptors, and thymocyte activation and development protein. For these and many other weakly homologous proteins, the homology lies in their Ig domains. As described below, B7L-1 proteins are expressed on brain tissue, dendritic cells, dendritic cell subsets and CD40 ligand-activated B cells.

The discovery of the DNA sequences disclosed in SEQ ID NOs: 1, 3 and 5 enables construction of expression vectors comprising DNAs encoding human and mouse B7L-1 proteins; host cells transfected or transformed with the expression vectors; biologically active B7L-1 as homogeneous proteins; and antibodies immunoreactive with B7L-1.

Since B7L-1 is found in bone marrow-derived and peripheral blood-monocyte derived dendritic cells, these molecules may be used to regulate inflammation in a therapeutic setting. The binding study results described in Example 13 show B7L-1 binding on tumor cell lines. Thus, biological signaling mediated by B7L1 could mediate functional anti tumor effects on these types of tumors.

As used herein, the term "B7L-1" refers to a genus of polypeptides that are binding proteins for LDCAM, novel polypeptides described in copending application Ser. No. 60/095,672 filed Aug. 7, 1998, and complex structures found in variety of cell lines including, but not limited to, lung epithelial cells, B lymphoblastoid cells and B cells. The term B7L-1 encompasses polypeptides having the amino acid sequence 1–432 of SEQ ID NO:2, the amino acid sequence 1–398 of SEQ ID NO:4; and amino acids 1–398 of SEQ ID NO:6. In addition, B7L-1 encompasses polypeptides that have a high degree of similarity or a high degree of identity with the amino acid sequence of SEQ ID NO:2, the amino acid sequence of SEQ ID NO:4, and amino acid sequence of SEQ ID NO:6, and which polypeptides are biologically active and bind their counterstructure, LDCAM.

The term "murine B7L-1" refers to biologically active gene products of the DNA of SEQ ID NO:3 and the term "human B7L-1" refers to biologically active gene products of the DNA of SEQ ID NO:1 and SEQ ID NO:5. Further encompassed by the term "B7L-1" are soluble or truncated proteins that include the binding portion of the protein and retain biological activity. Specific examples of such soluble proteins are those comprising the sequence of amino acids 1–364 of SEQ ID NO:2; those comprising the sequence of amino acids 1–330 of SEQ ID NO:4; and 1–330 of SEQ ID NO:6. Alternatively, such soluble proteins can exclude a leader sequence and thus encompass amino acids 21–364 of SEQ ID NO:2; amino acids 21–330 of SEQ ID NO:4; and amino acids 21–330 of SEQ ID NO:6.

The term "biologically active" as it refers to B7L-1, means that the B7L-1 is capable of binding to LDCAM, described in copending U.S. Patent Application Ser. No. 60/095,672 filed Aug. 7, 1998. LDCAM and B7L-1 are termed counterstructures because B7L-1 is a binding protein for LDCAM.

"Isolated" means that B7L-1 is free of association with other proteins or polypeptides, for example, as a purification product of recombinant host cell culture or as a purified extract.

A "B7L-1 variant" as referred to herein, means a polypeptide substantially homologous to native B7L-1, but which has an amino acid sequence different from that of native B7L-1 (human, murine or other mammalian species) because of one or more deletions, insertions or substitutions. The variant amino acid sequence preferably is at least 80% identical to a native B7L-1 amino acid sequence, most preferably at least 90% identical. The percent identity may be determined, for example, by comparing sequence information using the GAP computer program, version 6.0 described by Devereux et al. (*Nucl. Acids Res.* 12:387, 1984) and available from the University of Wisconsin Genetics Computer Group (UWGCG). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353–358, 1979; (2) a penalty of 3.0 for each gap and an additional 0.10 penalty for each symbol in each gap; and (3) no penalty for end gaps. Variants may comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Naturally occurring B7L-1 variants or alleles are also encompassed by the invention. Examples of such variants are proteins that result from alternate mRNA splicing events or from proteolytic cleavage of the B7L-1 protein, wherein the B7L-1 binding property is retained. Alternate splicing of mRNA may yield a truncated but biologically active B7L-1 protein, such as a naturally occurring soluble form of the protein, for example. Variations attributable to proteolysis include, for example, differences in the N- or C-termini upon expression in different types of host cells, due to proteolytic removal of one or more terminal amino acids from the B7L-1 protein (generally from 1–5 terminal amino acids).

As mentioned above, Example 1 describes identifying and isolating the complete coding region of human long extracellular B7L-1 DNA. This process involved searching a nucleotide sequence databank using a human B7-1 nucleotide sequence as the query sequence. Two expressed sequence tag (EST) files, GenBank accession numbers T08949 EST06841 and T32071 EST 43348, were identified has having homology with a portion of human B7-1. The GenBank record does not disclose a coding region for polypeptides encoded by these ESTs.

Example 5 describes the construction of a novel human B7L-1/Fc fusion protein that may be utilized in screening cell lines for binding to B7L-1 and in studying biological characteristics of B7L-1. Other antibody Fc regions may be substituted for the human IgG1 Fc region described in the Example. Other suitable Fc regions are those that can bind with high affinity to protein A or protein G, and include fragments of the human or murine IgG1 Fc region, e.g., fragments comprising at least the hinge region may be altered or mutated to a form having lower Fc receptor binding characteristics. The B7L-1/Fc fusion protein offers the advantage of being easily purified. Another advantage is the formation of disulfide bonds between the Fc regions of two separate fusion protein chains, thus creating dimers.

As described supra, an aspect of the invention is soluble B7L-1 polypeptides. Soluble B7L-1 polypeptides comprise all or part of the extracellular domain of a native B7L-1 but lack the signal that would cause retention of the polypeptide on a cell membrane. Soluble B7L-1 polypeptides advantageously comprise the native (or a heterologous) signal peptide when initially synthesized to promote secretion, but the signal peptide is cleaved upon secretion of B7L-1 from the cell. Soluble B7L-1 polypeptides encompassed by the invention retain at least one functional characteristic and in one embodiment are capable of binding a counterstructure described in copending application Ser. No. 60/095,672 filed Aug. 7, 1998. Indeed, soluble B7L-1 may also include part of the signal or part of the cytoplasmic domain or other sequences, provided that the soluble B7L-1 protein can be secreted.

Soluble B7L-1 may be identified (and distinguished from its non-soluble membrane-bound counterparts) by separating intact cells which express the desired protein from the culture medium, e.g., by centrifugation, and assaying the medium or supernatant for the presence of the desired protein. The presence of B7L-1 in the medium indicates that the protein was secreted from the cells and thus is a soluble form of the desired protein.

Soluble forms of B7L-1 possess many advantages over the native bound B7L-1 protein. Purification of the proteins from recombinant host cells is feasible, since the soluble proteins are secreted from the cells. Further, soluble proteins are generally more suitable for intravenous administration.

Examples of soluble B7L-1 polypeptides include those comprising a substantial portion of the extracellular domain of a native B7L-1 protein. An example of a soluble B7L-1 protein comprises amino acids 1–364 of SEQ ID NO:2 and amino acids 1–330 of SEQ ID NO:4, and 1–330 of SEQ ID NO:6. In addition, truncated soluble B7L-1 proteins comprising less than the entire extracellular domain are included in the invention. When initially expressed within a host cell, soluble B7L-1 may additionally comprise one of the heterologous signal peptides described below that is functional within the host cells employed. Alternatively, the protein may comprise the native signal peptide. In one embodiment of the invention, soluble B7L-1 can be expressed as a fusion protein comprising (from N- to C-terminus) the yeast α-factor signal peptide, a FLAG® peptide described below and in U.S. Pat. No. 5,011,912, and soluble B7L-1 consisting of amino acids 21–364 of SEQ ID NO:2 or 21–330 of SEQ ID NO:4, or 21–330 of SEQ ID NO:6. This recombinant fusion protein is expressed in and secreted from yeast cells. The FLAG® peptide facilitates purification of the protein, and subsequently may be cleaved from the soluble B7L-1 using bovine mucosal enterokinase. Isolated DNA sequences encoding soluble B7L-1 proteins are encompassed by the invention.

Truncated B7L-1, including soluble polypeptides, may be prepared by any of a number of conventional techniques. A desired DNA sequence may be chemically synthesized using techniques known per se. DNA fragments also may be produced by restriction endonuclease digestion of a full length cloned DNA sequence, and isolated by electrophoresis on agarose gels. Linkers containing restriction endonuclease cleavage site(s) may be employed to insert the desired DNA fragment into an expression vector, or the fragment may be digested at cleavage sites naturally present therein. The well known polymerase chain reaction procedure also may be employed to amplify a DNA sequence encoding a desired protein fragment. As a further alternative, known mutagenesis techniques may be employed to insert a stop codon at a desired point, e.g., immediately downstream of the codon for the last amino acid of the receptor-binding domain.

As stated above, the invention provides isolated or homogeneous B7L-1 polypeptides, both recombinant and non-recombinant. Variants and derivatives of native B7L-1 proteins that retain the desired biological activity (e.g., the ability to bind LDCAM) may be obtained by mutations of nucleotide sequences coding for native B7L-1 polypeptides. Alterations of the native amino acid sequence may be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene wherein predetermined codons can be altered by substitution, deletion or insertion. Exemplary methods of making the alterations set forth above are disclosed by Walder et al. (*Gene* 42:133, 1986); Bauer et al. (*Gene* 37:73, 1985); Craik (*BioTechniques*, Jan. 12–19, 1985); Smith et al. (*Genetic Engineering: Principles and Methods*, Plenum Press, 1981); Kunkel (*Proc. Natl. Acad. Sci. USA* 82:488, 1985); Kunkel et al. (*Methods in Enzymol.* 154:367, 1987); and U.S. Pat. Nos. 4,518,584 and 4,737,462 all of which are incorporated by reference.

B7L-1 may be modified to create B7L-1 derivatives by forming covalent or aggregative conjugates with other chemical moieties, such as glycosyl groups, lipids, phosphate, acetyl groups and the like. Covalent derivatives of B7L-1 may be prepared by linking the chemical moieties to functional groups on B7L-1 amino acid side chains or at the N-terminus or C-terminus of a B7L-1 polypeptide or the extracellular domain thereof. Other derivatives of B7L-1 within the scope of this invention include covalent or aggregative conjugates of B7L-1 or its fragments with other proteins or polypeptides, such as by synthesis in recombinant culture as N-terminal or C-terminal fusions. For example, the conjugate may comprise a signal or leader polypeptide sequence (e.g. the α-factor leader of Saccharomyces) at the N-terminus of a B7L-1 polypeptide. The signal or leader peptide co-translationally or post-translationally directs transfer of the conjugate from its site of synthesis to a site inside or outside of the cell membrane or cell wall.

B7L-1 polypeptide fusions can comprise peptides added to facilitate purification and identification of B7L-1. Such peptides include, for example, poly-His or the antigenic identification peptides described in U.S. Pat. No. 5,011,912 and in Hopp et al., *Bio/Technology* 6:1204, 1988.

The invention further includes B7L-1 polypeptides with or without associated native-pattern glycosylation. B7L-1 expressed in yeast or mammalian expression systems (e.g., COS-7 cells) may be similar to or significantly different from a native B7L-1 polypeptide in molecular weight and glycosylation pattern, depending upon the choice of expression system. Expression of B7L-1 polypeptides in bacterial expression systems, such as *E. coli*, provides non-glycosylated molecules.

Equivalent DNA constructs that encode various additions or substitutions of amino acid residues or sequences, or deletions of terminal or internal residues or sequences not needed for biological activity or binding are encompassed by the invention. For example, N-glycosylation sites in the B7L-1 extracellular domain can be modified to preclude glycosylation, allowing expression of a reduced carbohydrate analog in mammalian and yeast expression systems. N-glycosylation sites in eukaryotic polypeptides are characterized by an amino acid triplet Asn-X-Y, wherein X is any amino acid except Pro and Y is Ser or Thr. The murine B7L-1 and human B7L-1 proteins comprise two such triplets. In the human long extracellular B7L-1, glycosylation sites occur at amino acids 25–27 and at amino acids 324–326. In the murine short extracellular B7L-1 and the human short extracellular as shown in SEQ ID NO:6, glycosylation sites occur at amino acids 25–27 and at amino acids 290–292. Appropriate substitutions, additions or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Known procedures for inactivating N-glycosylation sites in proteins include those described in U.S. Pat. No. 5,071,972 and EP 276,846, hereby incorporated by reference.

In another example, sequences encoding Cys residues that are not essential for biological activity can be altered to cause the Cys residues to be deleted or replaced with other amino acids, preventing formation of incorrect intramolecular disulfide bridges upon renaturation. Other equivalents are prepared by modification of adjacent dibasic amino acid residues to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites. The human B7L-1 and murine B7L-1 contain one KEX2 protease processing site at amino acids 109–110 and 200–201 of SEQ ID NO:2 and amino acids 75–76 and 166–167 of SEQ ID NO:4 and SEQ ID NO:6.

Nucleic acid sequences within the scope of the invention include isolated DNA and RNA sequences that hybridize to the B7L-1 nucleotide sequences disclosed herein under conditions of moderate or severe stringency, and that encode biologically active B7L-1. Conditions of moderate stringency, as defined by Sambrook et al. *Molecular Cloning: A Laboratory Manual*, 2 ed. Vol. 1, pp. 101–104, Cold Spring Harbor Laboratory Press, (1989), include use of a prewashing solution of 5×SSC, 0.5% SDS, 1.0 mM EDTA (pH 8.0) and hybridization conditions of about 55° C., 5×SSC, overnight. Conditions of severe stringency include higher temperatures of hybridization and washing. The skilled artisan will recognize that the temperature and wash solution salt concentration may be adjusted as necessary according to factors such as the length of the nucleic acid molecule.

Due to the known degeneracy of the genetic code wherein more than one codon can encode the same amino acid, a DNA sequence may vary from that shown in SEQ ID NO:1, SEQ ID NO:3 and SEQ ID NO:5 and still encode a B7L-1 protein having the amino acid sequence of SEQ ID NO:2, SEQ ID NO:4 and SEQ ID NO:6, respectively. Such variant DNA sequences may result from silent mutations (e.g., occurring during PCR amplification), or may be the product of deliberate mutagenesis of a native sequence.

The invention provides equivalent isolated DNA sequences encoding biologically active B7L-1, selected from: (a) cDNA comprising the nucleotide sequence presented in SEQ ID NO:1, SEQ ID NO:3, or SEQ ID NO:5; (b) DNA capable of hybridization to a DNA of (a) under moderately stringent conditions and that encodes biologically active B7L-1; and, (c) DNA that is degenerate as a result of the genetic code to a DNA defined in (a), or (b) and that encodes biologically active B7L-1. B7L-1 proteins encoded by such DNA equivalent sequences are encompassed by the invention.

DNAs that are equivalents to the DNA sequence of SEQ ID NO:1, SEQ ID NO:3, or SEQ ID NO:5 will hybridize under moderately and severely stringent conditions to DNA sequences that encode polypeptides comprising SEQ ID NO:2, SEQ ID NO:4, SEQ ID NO:6 or fragments and variants of SEQ ID NO:2, 4, and 6. Examples of B7L-1 proteins encoded by such DNA, include, but are not limited to, B7L-1 fragments (soluble or membrane bound) and B7L-1 proteins comprising inactivated N-glycosylation site (s), inactivated KEX2 protease processing site(s), or conservative amino acid substitution(s), as described above.

B7L-1 proteins encoded by DNA derived from other mammalian species, wherein the DNA will hybridize to the cDNA of SEQ ID NO:1, SEQ ID NO:3, or SEQ ID NO:5 are also encompassed by the present invention.

Variants possessing the ability to bind B7L-1 counterstructures, or binding partners, e.g. LDCAM may be identified by any suitable assay. Biological activity of B7L-1 may be determined, for example, by competition for binding to the ligand binding domain of LDCAM (i.e. competitive binding assays).

One type of a competitive binding assay for a B7L-1 polypeptide uses a radiolabeled, soluble B7L-1 and intact cells expressing a B7L-1 counterstructure, or cells expressing LDCAM. Instead of intact cells, one could substitute soluble B7L-1 counterstructure Fc fusion proteins (such as a LDCAM/Fc fusion protein) bound to a solid phase through the interaction of a Protein A, Protein G or an antibody to the counterstructure or Fc portions of the molecule, with the Fc region of the fusion protein. Another type of competitive binding assay utilizes radiolabeled soluble B7L-1 binding proteins and intact cells expressing B7L-1.

Competitive binding assays can be performed following conventional methodology. For example, radiolabeled B7L-1 can be used to compete with a putative B7L-1 homologue to assay for binding activity against a surface-bound B7L-1 binding protein or a binding counterstructure, e.g. LDCAM. Qualitative results can be obtained by competitive autoradiographic plate binding assays, or Scatchard plots may be utilized to generate quantitative results.

Binding proteins for a B7L-1 counterstructure, such as B7L-1 itself and anti-B7L-1 ligand antibodies, can be bound to a solid phase such as a column chromatography matrix or a similar substrate suitable for identifying, separating or purifying cells that express the B7L-1 binding protein on their surface. Binding of a B7L-1 counterstructure binding protein to a solid phase contacting surface can be accomplished by using a number of different techniques. For example, a B7L-1/Fc fusion protein can be constructed and then attached to the solid phase through the interaction of Protein A or Protein G. Various other means for fixing proteins to a solid phase are well known in the art and are suitable arrogant for use in the present invention. For example, magnetic microspheres can be coated with B7L-1 and held in the incubation vessel through a magnetic field. Suspensions of cell mixtures containing a B7L-1 counterstructure-expressing cells are contacted with the solid phase that has B7L-1 polypeptides thereon. Cells having B7L-1 counterstructure on their surface bind to the fixed B7L-1 and unbound cells then are washed away. This affinity-binding method is useful for purifying, screening or separating such B7L-1 counterstructure-expressing cells from solution. In particular, this method is useful for separating cells expressing LDCAM from cells that do not express a B7L-1 binding protein or B7L-1 counter structure.

Methods of releasing positively selected cells from the solid phase are known in the art and encompass, for example, the use of enzymes. Such enzymes are preferably non-toxic and non-injurious to the cells and are preferably directed to cleaving the cell-surface binding partner. In the case of LDCAM-B7L-1 interactions, the enzyme preferably would cleave the LDCAM thereby freeing the resulting cell suspension from the "foreign" B7L-1 material.

Alternatively, mixtures of cells suspected of containing LDCAM+ cells first can be incubated with biotinylated B7L-1. Incubation periods are typically at least one hour in duration to ensure sufficient binding to B7L-1 The resulting mixture then is passed through a column packed with avidin-coated beads, whereby the high affinity of biotin for avidin provides the binding of the cell to the beads. Use of avidin-coated beads is known in the art. See Berenson, et al. *J. Cell. Biochem.,* 10D:239 (1986). Wash of unbound material and the release of the bound cells is performed using conventional methods.

As described above, B7L-1 can be used to separate cells expressing a protein to which it binds. In an alternative method, B7L-1 or an extracellular domain or a fragment thereof can be conjugated to a detectable moiety such as $^{125}I$ to detect cells expressing a B7L-1 binding protein. Radiolabeling with $^{125}I$ can be performed by any of several standard methodologies that yield a functional $^{125}I$-B7L-1 molecule labeled to high specific activity. Or an iodinated or biotinylated antibody against B7L-1 region or the Fc region of the molecule could be used. Another detectable moiety such as an enzyme that can catalyze a colorimetric or fluorometric reaction, biotin or avidin may be used. For example, cells to be tested for LDCAM expression can be contacted with labeled B7L-1. After incubation, unbound labeled B7L-1 is removed and binding is measured using the detectable moiety.

The binding characteristics of B7L-1, B7L-1 fragments and B7L-1 variants may also be determined using the a labeled B7L-1 binding protein (for example, $^{125}I$-LDCAM:Fc) in competition assays similar to those described above. In this case, however, intact cells expressing LDCAM bound to a solid substrate, are used to measure the extent to which a sample containing a putative B7L-1 variant competes for binding with a B7L-1 binding protein.

Other means of assaying for B7L-1 include the use of anti-B7L-1 antibodies, cell lines that proliferate in response to B7L-1, or recombinant cell lines that express LDCAM and proliferate in the presence of B7L-1.

The B7L-1 proteins disclosed herein also may be employed to measure the biological activity of LDCAM proteins in terms of their binding affinity for B7L-1. As one example, B7L-1 may be used in determining whether biological activity is retained after modification of a LDCAM (e.g., chemical modification, truncation, mutation, etc.). The biological activity of a LDCAM protein thus can be ascertained before it is used in a research study, or possibly in the clinic, for example.

B7L-1 proteins find use as reagents that may be employed by those conducting "quality assurance" studies, e.g., to monitor shelf life and stability of proteins to which B7L-1 binds under different conditions. To illustrate, B7L-1 may be employed in a binding affinity study to measure the biological activity of its binding protein that has been stored at different temperatures, or produced in different cell types. The binding affinity of the modified protein for B7L-1 is compared to that of an unmodified protein to detect any adverse impact of the modifications on biological activity of B7L-1 binding protein.

B7L-1 polypeptides also find use as carriers for delivering agents attached thereto to cells bearing its counter structure, LDCAM or other cell surface receptor to which B7L-1 binds. For example, soluble forms of B7L-1 can be conjugated to agents such as toxins, inhibitors, or antigens and the resulting conjugated agent can be delivered to cells carrying the B7L-1 counterstructure (LDCAM). Such cells include lymphoid dendritic cells that are known product IL-12 during an immune response and can inhibit T cell cytokine production. Thus, these cells are a target for induction of antigen tolerance and B7L-1 conjugates can be used to block, enhance or modify lymphoid dendritic cell activity.

Diagnostic and therapeutic agents that may be attached to a B7L-1 polypeptide include, but are not limited to, drugs, toxins, radionuclides, chromophores, enzymes that catalyze a colorimetric or fluorometric reaction, and the like, with the particular agent being chosen according to the intended application. Examples of drugs include those used in treating various forms of cancer, e.g., nitrogen mustards such as L-phenylalanine nitrogen mustard or cyclophosphamide, intercalating agents such as cis-diaminodichloroplatinum, antimetabolites such as 5-fluorouracil, vinca alkaloids such as vincristine, and antibiotics such as bleomycin, doxorubicin, daunorubicin, and derivatives thereof. Among the toxins are ricin, abrin, diptheria toxin, *Pseudomonas aeruginosa* exotoxin A, ribosomal inactivating proteins, mycotoxins such as trichothecenes, and derivatives and fragments (e.g., single chains) thereof. Radionuclides suitable for diagnostic use include, but are not limited to, $^{123}$I, $^{131}$I, $^{99m}$Tc, $^{111}$In, and $^{76}$Br. Radionuclides suitable for therapeutic use include, but are not limited to, $^{131}$I, $^{211}$At, $^{77}$Br, $^{186}$Re, $^{188}$Re, $^{212}$Pb, $^{212}$Bi, $^{109}$Pd, $^{64}$Cu, and $^{67}$Cu.

Such agents may be attached to the B7L-1 by any suitable conventional procedure. B7L-1, being a protein, comprises functional groups on amino acid side chains that can be reacted with functional groups on a desired agent to form covalent bonds, for example. Alternatively, the protein or agent may be derivatized to generate or attach a desired reactive functional group. The derivatization may involve attachment of one of the bifunctional coupling reagents available for attaching various molecules to proteins (Pierce Chemical Company, Rockford, Ill.). A number of techniques for radiolabeling proteins are known. Radionuclide metals may be attached to B7L-1 by using a suitable bifunctional chelating agent, for example.

Conjugates comprising B7L-1 and a suitable diagnostic or therapeutic agent (preferably covalently linked) are thus prepared. The conjugates are administered or otherwise employed in an amount appropriate for the particular application.

Another use of the B7L-1 of the present invention is as a research tool for studying the role that B7L-1, in conjunction with LDCAM, may play in T cell signaling and proliferation. The B7L-1 polypeptides of the present invention also may be employed in in vitro assays for detection of LDCAM or B7L-1 or the interactions thereof.

As discussed above, when various tissues were analyzed for mRNA for B7L-1, transcripts were detected in human bone marrow derived CD34+ derived dendritic cells and peripheral blood derived dendritic cells, B cells after stimulation with CD40L, brain and mouse splenic dendritic cells CD40L stimulated splenic B cells and brain. Because of the restricted expression pattern of B7L-1, antibodies to B7L-1 can be used to identify, isolate, and purify potent antigen presenting cells, including dendritic cells and CD40 ligand activated B cells. Additionally, the presence and level of mRNA for B7L-1 can be exploited to determine the purity of bone marrow derived and blood derived dendritic cell preparations. Other uses of antibodies to B7L-1 molecules include targeting antigens to myeloid dendritic cells or eliminating myeloid dendritic cells with anti-B7L-1 antibody mediated depletion or with an conjugate of a toxin and the antibody.

Soluble fragments of B7L-1, including, but not restricted to the extracellular domains of SEQ ID NO:2, SEQ ID NO:4, and SEQ ID NO:6 can be used to enhance or inhibit the activity of lymphoid dendritic cells and/or B cells activated for presentation by CD40-L.

One embodiment of the present invention is directed to a method of treating disorders mediated by the interaction of B7L-1 and a binding partner and involves administering B7L-1 to a mammal having the disorder. B7L-1 polypeptides of the invention can be formulated according to known methods used to prepare pharmaceutically useful compositions. B7L-1 can be combined in admixture, either as the sole active material or with other known active materials, with pharmaceutically suitable diluents (e.g., Tris-HCl, acetate, phosphate), preservatives (e.g., Thimerosal, benzyl alcohol, parabens), emulsifiers, solubilizers, adjuvants and/or carriers. Suitable carriers and their formulations are described in Remington's Pharmaceutical Sciences, 16th ed. 1980, Mack Publishing Co. In addition, such compositions can contain B7L-1 complexed with polyethylene glycol (PEG), metal ions, or incorporated into polymeric compounds such as polyacetic acid, polyglycolic acid, hydrogels, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance of B7L-1. B7L-1 can also be conjugated to antibodies against tissue-specific receptors, ligands or antigens, or coupled to ligands of tissue-specific receptors. For tumor cells on which LDCAM is found, B7L-1 may be conjugated to a toxin whereby B7L-1 is used to deliver the toxin to the specific cell site.

B7L-1 can be administered topically, parenterally, or by inhalation. The term "parenteral" includes subcutaneous injections, intravenous, intramuscular, intracisternal injection, or infusion techniques. These compositions will typically contain an effective amount of the B7L-1, alone or in combination with an effective amount of any other active material. Such dosages and desired drug concentrations contained in the compositions may vary depending upon many factors, including the intended use, patient's body weight and age, and route of administration. Preliminary doses can be determined according to animal tests, and the scaling of dosages for human administration can be performed according to art-accepted practices.

B7L-1 polypeptides may exist as oligomers, such as covalently-linked or non-covalently-linked dimers or trimers. Oligomers may be linked by disulfide bonds formed between cysteine residues on different B7L-1 polypeptides. In one embodiment of the invention, a B7L-1 dimer is created by fusing B7L-1 to the Fc region of an antibody (e.g., IgG1) in a manner that does not interfere with binding of B7L-1 to the B7L-1 ligand-binding domain. The Fc polypeptide preferably is fused to the C-terminus of a soluble B7L-1 (comprising only the receptor-binding). General preparation of fusion proteins comprising heterologous polypeptides fused to various portions of antibody-derived polypeptides (including the Fc domain) has been described, e.g., by Ashkenazi et al. (*PNAS USA* 88:10535, 1991) and Byrn et al. (*Nature* 344:677, 1990), hereby incorporated by reference. A gene fusion encoding the B7L-1:Fc fusion protein is inserted into an appropriate expression vector. B7L-1:Fc fusion proteins are allowed to assemble much like antibody molecules, whereupon interchain disulfide bonds form between Fc polypeptides, yielding divalent B7L-1. If fusion proteins are made with both heavy and light chains of an antibody, it is possible to form a B7L-1 oligomer with as many as four B7L-1 extracellular regions. Alternatively, one can link two soluble B7L-1 domains with a peptide linker.

Suitable host cells for expression of B7L-1 polypeptides include prokaryotes, yeast or higher eukaryotic cells. Appropriate cloning and expression vectors for use with bacterial, fungal, yeast, and mammalian cellular hosts are described, for example, in Pouwels et al. *Cloning Vectors: A Laboratory Manual*, Elsevier, N.Y., (1985). Cell-free translation systems could also be employed to produce B7L-1 polypeptides using RNAs derived from DNA constructs disclosed herein.

Prokaryotes include gram negative or gram positive organisms, for example, *E. coli* or Bacilli. Suitable prokaryotic host cells for transformation include, for example, *E. coli, Bacillus subtilis, Salmonella typhimurium*, and various other species within the genera Pseudomonas, Streptomyces, and Staphylococcus. In a prokaryotic host cell, such as *E. coli*, a B7L-1 polypeptide may include an N-terminal methionine residue to facilitate expression of the recombinant polypeptide in the prokaryotic host cell. The N-terminal Met may be cleaved from the expressed recombinant B7L-1 polypeptide.

B7L-1 polypeptides may be expressed in yeast host cells, preferably from the Saccharomyces genus (e.g., *S. cerevisiae*). Other genera of yeast, such as Pichia, *K. lactis* or Kluyveromyces, may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73,657 or in Fleer et. al., *Gene*, 107:285–195 (1991); and van den Berg et. al., *Bio/Technology*, 8:135–139 (1990). Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA sequences from pBR322 for selection and replication in *E. coli* (Amp$^r$ gene and origin of replication) into the above-described yeast vectors.

The yeast α-factor leader sequence may be employed to direct secretion of the B7L-1 polypeptide. The α-factor leader sequence is often inserted between the promoter sequence and the structural gene sequence. See, e.g., Kurjan et al., *Cell* 30:933, 1982; Bitter et al., *Proc. Natl. Acad. Sci. USA* 81:5330, 1984; U. S. Pat. No. 4,546,082; and EP 324,274. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for Trp$^+$ transformants in a selective medium, wherein the selective medium consists of 0.67% yeast nitrogen base, 0.5% casamino acids, 2% glucose, 10 μg/ml adenine and 20 μg/ml uracil.

Yeast host cells transformed by vectors containing ADH2 promoter sequence may be grown for inducing expression in a "rich" medium. An example of a rich medium is one consisting of 1% yeast extract, 2% peptone, and 1% glucose supplemented with 80 μg/ml adenine and 80 μg/ml uracil. Derepression of the ADH2 promoter occurs when glucose is exhausted from the medium.

Mammalian or insect host cell culture systems could also be employed to express recombinant B7L-1 polypeptides. Baculovirus systems for production of heterologous proteins in insect cells are reviewed by Luckow and Summers, *Bio/Technology* 6:47 (1988). Established cell lines of mammalian origin also may be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV-1/EBNA-1 cell line derived from the African green monkey kidney cell line CVI (ATCC CCL 70) as described by McMahan et al. (*EMBO J.* 10: 2821, 1991).

Transcriptional and translational control sequences for mammalian host cell expression vectors may be excised from viral genomes. Commonly used promoter sequences and enhancer sequences are derived from Polyoma virus, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide other genetic elements for expression of a structural gene sequence in a mammalian host cell. Viral early and late promoters are particularly useful because both are easily obtained from a viral genome as a fragment which may also contain a viral origin of replication (Fiers et al., *Nature* 273:113, 1978). Smaller or larger SV40 fragments may also be used, provided the approximately 250 bp sequence extending from the Hind III site toward the Bgl I site located in the SV40 viral origin of replication site is included.

Exemplary expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells can be constructed substantially as described by Cosman et al. (*Mol. Immunol.* 35 23:935, 1986). A useful high expression vector, PMLSV N1I/N4, described by Cosman et al., *Nature* 312:768, 1984 has been deposited as ATCC 39890. Additional useful mammalian expression vectors are described in EP-A-0367566, and in U.S. Patent Application Ser. No. 07/701,415, filed May 16, 1991, incorporated by reference herein. The vectors may be derived from retroviruses. In place of the native signal sequence, and in addition to an initiator methionine, a heterologous signal sequence may be added, such as the signal sequence for IL-7 described in U.S. Pat. No. 4,965, 195; the signal sequence for IL-2 receptor described in Cosman et al., *Nature* 312:768 (1984); the IL-4 signal peptide described in EP 367,566; the type I IL-1 receptor signal peptide described in U.S. Pat. No. 4,968,607; and the type II IL-1 receptor signal peptide described in EP 460,846.

B7L-1 as an isolated, purified or homogeneous protein according to the invention may be produced by recombinant expression systems as described above or purified from naturally occurring cells. B7L-1 can be purified to substantial homogeneity, as indicated by a single protein band upon analysis by SDS-polyacrylamide gel electrophoresis (SDS-PAGE).

One process for producing B7L-1 comprises culturing a host cell transformed with an expression vector comprising a DNA sequence that encodes B7L-1 under conditions sufficient to promote expression of B7L-1. B7L-1 is then recovered from culture medium or cell extracts, depending upon the expression system employed. As is known to the skilled artisan, procedures for purifying a recombinant protein will vary according to such factors as the type of host cells employed and whether or not the recombinant protein is secreted into the culture medium.

For example, when expression systems that secrete the recombinant protein are employed, the culture medium first may be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Finally, one or more reversed-phase high performance liquid chromatography (RP-HPLC) steps employing hydrophobic RP-HPLC media, (e.g., silica gel having pendant methyl or other aliphatic groups) can be employed to further purify B7L-1. Some or all of the foregoing purification steps, in various combinations, are well known and can be employed to provide a substantially homogeneous recombinant protein.

It is possible to utilize an affinity column comprising the B7L-1 binding domain of a protein to which B7L-1 binds, such as LDCAM, to affinity-purify expressed B7L-1 polypeptides. B7L-1 polypeptides can be removed from an affinity column using conventional techniques, e.g., in a high salt elution buffer and then dialyzed into a lower salt buffer for use or by changing pH or other components depending on the affinity matrix utilized. Alternatively, the affinity column may comprise an antibody that binds B7L-1. Example 5 describes a procedure for employing B7L-1 of the invention to generate monoclonal antibodies directed against B7L-1.

Recombinant protein produced in bacterial culture can be isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

Transformed yeast host cells are preferably employed to express B7L-1 as a secreted polypeptide in order to simplify purification. Secreted recombinant polypeptide from a yeast host cell fermentation can be purified by methods analogous to those disclosed by Urdal et al. (*J. Chromatog.* 296:171, 1984). Urdal et al. describe two sequential, reversed-phase HPLC steps for purification of recombinant human IL-2 on a preparative HPLC column.

Useful fragments of the B7L-1 nucleic acids include antisense or sense oligonucleotides comprising a single-stranded nucleic acid sequence (either RNA or DNA) capable of binding to target B7L-1 mRNA (sense) or B7L-1 DNA (antisense) sequences. Antisense or sense oligonucleotides, according to the present invention, comprise a fragment of the coding region of B7L-1 cDNA. Such a fragment generally comprises at least about 14 nucleotides, preferably from about 14 to about 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides thus may be used to block expression of B7L-1 proteins. Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences. Other examples of sense or antisense oligonucleotides include those oligonucleotides which are covalently linked to organic moieties, such as those described in WO 90/10448, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. Antisense or sense oligonucleotides are preferably introduced into a cell containing the target nucleic acid sequence by insertion of the antisense or sense oligonucleotide into a suitable retroviral vector, then contacting the cell with the retrovirus vector containing the inserted sequence, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see PCT Application US 90/02656).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

In addition to the above, the following examples are provided to illustrate particular embodiments and not to limit the scope of the invention.

EXAMPLE 1

Identifying human B7L-1 Long Extracellular Form

The DNA encoding human B7-1, a T cell costimulatory molecule and a SMARTLIST protein, was used in a BLAST sequence analysis to identify ESTs having homology to B7-1. This BLAST analysis resulted in the identification of two GENBANK ESTs, File No. T08949 (EST06841) and File No. T32071 (EST 43348), TIGR, having low but significant homology to a portion of the B7-1 molecule.

The two GENBANK EST sequences were used to design PCR primers for probing cDNA libraries in order to identify a cDNA source for the ESTs. The primer sequences were as follows:

5' AGGGCGAGTACACCTG 3' (SEQ ID NO:7) (sense bases 22–37 of EST T32071)

5' GTGGATCTGTCAGCTCC 3' (SEQ ID NO:8) (anti-sense bases 376–360 of EST T32071)

Oligonucleotide primers identified in SEQ ID NO:7 and SEQ ID NO:8 were used to screen cDNA libraries by PCR. Of the 16 cDNA libraries examined, PCR product was obtained only from a human brain lambda library (purchased from Clonetech HL3002b). The product was cloned into bacteria and sequenced to verify that the product included an open reading frame.

The cloned EST sequence was radioactively labeled and used to probe the brain lambda library using standard probing techniques, in order to isolate clones from the brain lambda library that included the EST derived sequence. One clone, designated 32071-2, extended the EST sequence to the 5' end by 140 bases. A subsequent BLAST analysis of the GENBANK EST database using the extended EST sequence as the query sequence lead to the identification of an overlapping EST (H15268) derived from IMAGE Consortium clone #44904.

The IMAGE Consortium clone was obtained (Research Genetics, 07002) and fully sequenced to reveal an open reading frame and a new full length human cDNA sequence encoding B7L-1. SEQ ID NO:1 provides the complete cDNA of human B7L-1 and SEQ ID NO:2 provides the amino acid sequence encoded by the cDNA. The encoded full length protein has a predicted extracellular region of amino acid 364 amino acids (1–364), including a leader sequence of 20 amino acids (1–20); a transmembrane domain of 21 amino acids (365–385) and a cytoplasmic domain of 47 amino acids (386–432).

EXAMPLE 2

Expressing Human Long Extracellular B7L-1

To prepare a vector construct for expressing human long extracellular B7L-1, the entire coding region of SEQ ID NO:1 was obtained from clone #49904. First, the B7L-1 insert was excised from the clone using the HindIII and NotI sites on the clone. Then the oligonucleotides identified in SEQ ID NO:9 and SEQ ID NO:10 were used as adapters to change the HindIII cohesive end to a SalI cohesive end by annealing and ligating the oligonucleotides to the excised insert containing nucleotide residues 1–1820 of SEQ ID NO:1. The resulting construct was ligated into a pDC409 expression vector that had been cut with SalI and NotI.

The expression vector construct was then transfected in CV1/EBNA cells and B7L-1 was expressed using techniques described in McMahan et al., *EMBO J.* 10:2821, 1991.

After the cells were shocked and incubated for several days, cell supernatants containing any soluble form of the protein were collected and the B7L-1 protein was recovered using HPLC techniques. To recover forms of B7L-1 that are membrane bound, the transfected cells were harvested, fixed in 1% paraformaldehyde, washed and used in their intact form.

EXAMPLE 3

Isolating Murine and Human Short Extracellular B7L-1

To identify a cDNA source of murine B7L-1, sequence information obtained from the human B7L-1 identified in EXAMPLE 1 above was used to design PCR primers, one of which is the oligonucleotides of SEQ ID NO:12; the second of which is disclosed in SEQ ID NO:13. These PCR primers were used to identify cDNA libraries that give PCR products when used as templates in PCR reactions. PCR product was identified in PCR reactions using mouse brain lambda cDNA library (Clonetech ML3000a).

The mouse brain lambda cDNA library was screened and a clone was identified and sequenced using standard techniques. The sequenced clone lacked the 5' end of the coding region as determined by comparing the clone with the human B7L-1. RT-PCR off of mouse brain RNA using the lambda gt10 vector entry oligonucleotide and the human B7L-1 specific oligonucleotide of SEQ ID NO:7 extended the sequence from the 3' to the end of the sequence and 5' to nearly full length. The clone encodes an open reading frame that begins at a position analogous to amino acid residue 9 of human B7L-1 (SEQ ID NO:2) and terminates at a position that is analogous to the terminal amino acid of the human B7L-1. The cloned murine B7L-1 cDNA having a composite murine/human leader is provided in SEQ ID NO:3 and its encoded polypeptide is provided in SEQ ID NO:4. The composite murine/human leader sequence includes 7 amino acids of the human sequence and 12 amino acids of the murine sequence. The murine B7L-1 clone is 95% identical to the human B7L-1 of SEQ ID NO:1 as determined by the GCG GAP program. The murine clone has a single gap and represents a shorter splice variant of B7L-1.

To investigate the existence of a human shorter splice variant of B7L-1, the oligonucleotide primers disclosed in SEQ ID NO:14 and SEQ ID NO:15 were used in RT-PCR reactions to probe human brain RNA. Using standard ethidium bromide agarose gel and Southern Blot analyses methodologies, a shorter splice form was shown to exist and predominate. The product of the RT-PCR reaction was cloned and subjected to standard dideoxynucleotide terminator sequence analysis. SEQ ID NO:5 provides the nucleotide sequence of the human short extracellular form of B7L-1 and SEQ ID NO:6 provides the encoded amino acid sequence.

The results of this work indicate that there are at least 2 different splice forms of B7L-1 and the predominant form is the short form which was first identified while cloning the murine B7L-1 homologue.

EXAMPLE 4

Expressing Murine Short Extracellular Form B7L-1 Polypeptide

The following describes methods for expressing a soluble fragment and the full length membrane bound murine short extracellular form of B7L-1.

To prepare a vector construct for expressing the full length membrane bound murine short extracellular form of B7L-1 the coding region of SEQ ID NO:3 was prepared using a PCR SOEing technique. The oligonucleotides used are described in SEQ ID NO:16, SEQ ID NO:17 and SEQ ID NO:18. The inner 5' oligonucleotide (SEQ ID NO:16) included bases to code for the initiator Met and 5 additional amino acids that form the first 6 residues of the long extracellular human B7L-1 signal peptide. The outer 5' oligonucleotide (SEQ ID NO17) was present in a 9 fold excess to the inner 5' oligonucleotide and included a SalI restriction site. The 3' oligonucleotide, described in SEQ ID NO:18, included a NotI restriction site.

The PCR SOEing product was subjected to a restriction enzyme digest with SalI and NotI and then ligated into a pDC412 expression vector. The expression vector was then transfected in DH10B *E coli* by electroporation.

B7L-1 was expressed using techniques described in McMahan et al., *EMBO J.* 10:2821,1991. To recover forms of B7L-1 that are membrane bound, the transfected cells were harvested, fixed in 1% paraformaldehyde, washed and used in their intact form.

To prepare a vector construct for expressing a soluble murine short extracellular B7L-1 polypeptide, the extracellular coding region of SEQ ID NO:3 was prepared using a PCR SOEing technique. The oligonucleotides used were identical to those used to prepare the vector construct for the murine full length membrane bound polypeptide except that the oligonucleotide of SEQ ID NO:12 was the 3' oligonucleotide, thus replacing SEQ ID NO:18.

The PCR SOEing product was subjected to a restriction enzyme digest with the SalI and BglII sites and then ligated into a Bluescript SK vector. This clone fusion was excised with a SalI//BglII double digestion and ligated into a SalI/BglII digested pDC412 expression vector. The expression vector was then transfected in DH10B *E coli* by electroporation and the soluble murine B7L-1 polypeptide was expressed as described above for the full length murine B7L-1 protein.

EXAMPLE 5

Preparing B7L-1/Fc Fusion Protein

The following describes generating a human B7L-1/Fc protein which was used to study binding characteristics of B7L-1. The fusion protein includes the predicted extracellular region of human B7L-1 and the mutein human Fc region.

To isolate the nucleotides that encode the extracellular domain of SEQ ID NO:2 (nucleotides 108–1249 of SEQ ID NO:1), oligonucleotides that flank the extracellular region of B7L-1 (SEQ ID NO:11 and SEQ ID NO:12) were used as primers in a PCR reaction to obtain a PCR product from clone #44904 which was the template in the reaction. The resulting PCR product was digested with SalI and BglII restriction enzymes at the SalI and BglII sites incorporated by the primers. The resulting fragment was ligated into an expression vector (pDC409) containing the human IgG1 Fc region mutated to lower Fc receptor binding.

The resulting DNA construct was transfected into the monkey kidney cell lines CV-1/EBNA (with co-transfection of psv3neo). After 7 days of culture in medium containing 0.5% low immunoglobulin bovine serum, a solution of 0.2% azide was added to the supernatant and the supernatant was filtered through a 0.22 μm filter. Then approximately 1 L of culture supernatant was passed through a BioCad Protein A HPLC protein purification system using a 4.6×100 mm Protein A column (POROS 20A from PerSeptive Biosystems) at 10 mL/min. The Protein A column binds the Fc Portion of the fusion protein in the supernatant, immobilizing the fusion protein and allowing other components of the supernatant to pass through the column. The column was washed with 30 mL of PBS solution and bound fusion protein was eluted from the HPLC column with citric acid adjusted to pH 3.0. Eluted purified fusion protein was neutralized as it eluted using 1M HEPES solution at pH 7.4.

EXAMPLE 6

Preparing Murine Short Extracellular B7L-1 Fc Fusion Protein

The following describes preparing a murine Fc fusion protein that included the soluble extracellular portion of the murine short extracellular B7L-1 and the mutein Fc peptide described above in Example 5. The extracellular domain coding region of the murine extracellular short B7L-1 was excised from the vector described in Example 4 using SaI and BglII restriction enzymes. The excised fragment was ligated into a pDC412 expression vector that included the human IgG1Fc region.

The resulting DNA construct was transfected into the monkey kidney cell lines CV-1/EBNA. The cells were cultured and the fusion protein collected and purified as described in Example 5.

EXAMPLE 7

Preparing B7L-1/polyHis Fusion Protein

The following describes preparing a human B7L-1/polyHis fusion protein (B7L-1/polyHis). The process included preparing a DNA construct that encodes the fusion protein, transfecting a cell line with the DNA construct, and harvesting supernatants from the transfected cells.

The oligonucleotide primers described in SEQ ID NO:12 and SEQ ID NO:13, containing a SpeI restriction site, were used to isolate the nucleotides encoding amino acids 1–364 of SEQ ID NO:2 from the IMAGE Consortium clone (H15268, clone #49904). The PCR product was digested with SpeI and PstI restriction enzymes, the PstI enzyme cutting the PCR product at a site within the B7L-1 coding region. The excised product was ligated into a SpeI/PstI digested Bluescript based vector containing a CMV viral leader upstream and in-frame with the SpeI site. The viral leader and the B7L-1 encoding cDNA construct was excised from the vector using SalI and PstI restriction enzyme digestions and the excised construct was then ligated in a three way ligation with a PstI/NotI fragment containing the remainder of the human B7L-1 cDNA and a pDC409 expression vector (McMahon et al., *EMBO J.* 10:2821, 1991).

The polyHis fusion construct was prepared using an oligonucleotide primer that primes upstream in the vector prepared as described above and a primer which includes 1) nucleotides complementary to those present in human B7L-1 cDNA that are positioned just before the transmembrane domain; 2) nucleotides complementary to the polyHis nucleotides; and, a NotI site. The polyHis containing fragment was digested with SalI and NotI and then ligated into a similarly digested pDC409 vector.

The resulting DNA fusion construct was transiently transfected into the monkey cell line COS-1 (ATCC CRL-1650). Following a 7 day culture in medium containing 0.5% low immunoglobulin bovine serum, cell supernatants were harvested and a solution of 0.2% sodium azide was added to the supernatants. The supernatants were filtered through a 0.22 µm filter, concentrated 10 fold with a prep scale concentrator (Millipore; Bedford, Mass.) and purified on a BioCad HPLC protein purification equipped with a Nickel NTA Superflow self pack resin column (Qiagen, Santa Clarita, Calif.). After the supernatant passed through the column, the column was washed with Buffer A (20 mM NaPO4, pH7.4; 300 mMNaCl; 50 mM Imidazole). Bound protein was then eluted from the column using a gradient elution techniques. Fractions containing protein were collected and analyzed on a 4–20% SDS-PAGE reducing gel. Fractions containing soluble B7L-1/polyHis fusion protein were pooled, concentrated 2 fold, and then dialyzed in PBS. The resulting soluble B7L-1/polyHis fusion protein was then filtered through a 0.22 µm sterile filter.

EXAMPLE 8

Screening Cell Lines for Binding to B7L-1

The B7L-1/Fc fusion protein prepared as described in Example 5 was used to screen cell lines for binding using quantitative binding studies according to standard flow cytometry methodologies. For each cell line screened, the procedure involved incubating approximately 250,000 to 1,000,000 of the cells blocked with 2% FCS (fetal calf serum), 5% normal goat serum and 5% rabbit serum in PBS for 1 hour. Then the blocked cells were incubated with 5 µg/mL of B7L-1/Fc fusion protein in 2% FCS, 5% goat serum and 5% rabbit serum in PBS. Following the incubation the sample was washed 2 times with FACS buffer (2% FCS in PBS) and then treated with mouse anti human Fc/biotin (purchased from Jackson Research) and SAPE (streptavidin-phycoerythrin purchased from Molecular Probes). This treatment causes the antihuman Fc/biotin to bind to any bound B7L-1/Fc and the SAPE to bind to the anti-human Fc/biotin resulting in a fluorescent identifying label on B7L-1/Fc which is bound to cells. The cells were analyzed for any bound protein using fluorescent detection flow cytometry. The results indicated that human B7L-1 binds well to human lung epithelial line (WI-26), human B lymphoblastoid lines (Daudi and PAE8LBM1, human fresh tonsillar B cells, murine $CD8^+$ dendritic cells from spleens/lymph nodes of flt3-L treated animals and murine T cell lymphoma (S49.1).

EXAMPLE 9

Preparing Monoclonal Antibodies to B7L-1

This example illustrates a method for preparing monoclonal antibodies to B7L-1. Purified B7L-1, a fragment thereof such as the extracellular domain, synthetic peptides or cells that express B7L-1 can be used to generate monoclonal antibodies against B7L-1 using conventional techniques, for example, those techniques described in U.S. Pat. No. 4,411,993. Briefly, rodents are immunized with B7L-1 as an immunogen emulsified in complete Freund's adjuvant, and injected in amounts ranging from 10–100 µg subcutaneously or intraperitoneally. Ten to twelve days later, the immunized animals are boosted with additional B7L-1 emulsified in incomplete Freund's adjuvant. The animals are periodically boosted thereafter on a weekly to bi-weekly immunization schedule. Serum samples are periodically taken by retro-orbital bleeding or tail-tip excision to test for B7L-1 antibodies by dot blot assay, ELISA (Enzyme-Linked Immunosorbent Assay), immunoprecipitation, or other suitable assays, including FACS analysis.

Following detection of an appropriate antibody titer, positive animals are provided one last intravenous injection of B7L-1 in saline. Three to four days later, the animals are sacrificed, spleen cells harvested, and spleen cells are fused to a murine myeloma cell line, e.g., NS1 or preferably P3x63Ag8.653 (ATCC CRL 1580). Fusions generate hybridoma cells, which are plated in multiple microtiter plates in a HAT (hypoxanthine, aminopterin and thymidine) selective medium to inhibit proliferation of non-fused cells, myeloma hybrids, and spleen cell hybrids.

The hybridoma cells are screened by ELISA for reactivity against purified B7L-1 by adaptations of the techniques disclosed in Engvall et al., *Immunochem.* 8:871, 1971 and in U.S. Pat. No. 4,703,004. A preferred screening technique is the antibody capture technique described in Beckmann et al., (*J. Immunol.* 144:4212, 1990) Positive hybridoma cells can be injected intraperitoneally into syngeneic BALB/c mice to produce ascites containing high concentrations of anti-B7L-1-L monoclonal antibodies. Alternatively, hybridoma cells can be grown in vitro in flasks or roller bottles by various techniques. Monoclonal antibodies produced in mouse ascites can be purified by ammonium sulfate precipitation, followed by gel exclusion chromatography. Alternatively, affinity chromatography based upon binding of antibody to protein A or protein G can also be used, as can affinity chromatography based upon binding to B7L-1.

EXAMPLE 10

Determining Tissue and Cells that Express Human and Murine B7L-1

The following describes RT-PCR and Northern Blot experiments that were carried out to identify tissue and cell types that express human and murine B7L-1 polypeptides of the present invention.

The RT-PCR process involved the reverse transcription of about 1 µg of total RNA from various human tissue and cell sources to make a first strand cDNA using the Pharmacia, First Strand cDNA Synthesis Kit following the manufacturer's instructions. Cell lines from which total RNA was transcribed included dendritic cells derived from human bone marrow; CD34+ cells and CD34– cells; human peripheral blood B cells cultured in IL-4, SAC or CD40L; human monocyte derived dendritic cells; human monocytes cultured in IFN gamma; human and mouse brain; mouse splenic B cells cultured +/–CD40L; mouse splenic T cells +/–ConA stimulation.

The RT-PCR results indicated that B7L-1 is expressed by human bone marrow CD34+ derived and peripheral blood derived dendritic cells and human peripheral blood B cells after stimulation with CD40L. Additionally mRNA was found in brain and a weak PCR signal was found in CD34-bone marrow cells. The results showed that murine B7L-1 is expressed in murine splenic dendritic cells, CD40L stimulated splenic B cells, and in murine brain.

Northern Blot analysis was performed by fractionating 5 µg or 10 µg total RNA on 1.2% agarose gels containing formaldehyde. The RNA was then blotted onto Hybond Nylon membranes using standard blotting techniques. Poly A+ multiple tissue blots containing 1 µg of mouse mRNA from a number of different sources were purchased from Clonetech. The purchased blots were prehybridized according to manufacturer's instructions for at least 6 hours at 68° C. Riboprobes, containing the coding region of murine B7L-1, were generated using Promega's Riboprobe Combination Kit and T7 RNA Polymerase according to the manufacturer's instructions. Standard Northern Blot generating procedures as described in Maniatis, (*Molecular Clon-* ing: a Laboratory Manual, Cold Spring Harbor Lab. Press, 1989) were used.

The results of probing the Northern blots with the riboprobes and visualizing the resulting x-ray film for positively binding probes show that hybridizing RNA was detected in brain, liver, skeletal muscle and heart. In the brain, two band sizes were observed. One RNA was approximately 4.0 kB and the other approximately 2.7 kB. In the liver the predominate band indicated hybridizing RNA of mostly 2.7 kB and in the skeletal muscle and heart only the 2.7 kB RNA band was observed.

EXAMPLE 11

Cell Binding Studies

In order to study binding to murine NK cells, spleens were removed from IL-15 treated CB-17/SCID mice and used as a source for highly enriched and activated murine NK cells. Spleen cells isolated from IL-15 treated SCID mice are 60–80% DX-5 positive. DX-5 is a pan NK marker than is expressed on NK cells from many different strains of mice. Flow cytometric analysis was performed to detect B7L1 and LDCAM binding to DX-5+ in vivo IL-15 activated murine NK cells. Table I gives the results of a murine NK cell binding study.

TABLE I

| Fc molecule | DX-5 + NK cell % +/MFI |
|---|---|
| control Fc | 8%/88 |
| B7L1Fc | 19%/265 |
| LDCAM Fc | 38%/432 |

LDCAM and B7L1 binding can be detected on in vivo activated murine NK cells.

Results of experiments directed at studying B7L1 and LDCAM binding to human endothelial cells demonstrated no binding on human umbilical vein endothelial cells (HUVEC) from different donors. However, for a HUVEC from one donor, B7L1 did induce low levels of CD62E and CD106 compared to control Fc.

EXAMPLE 12

Isolating a Counterstructure that Binds B7L-1

Based upon the results of the binding experiments described in Example 8, cDNA pools from a WI-26 cell line expression library were screened for binding to the purified B7L-1/Fc fusion protein prepared as described in Example 5. The expression library was prepared using standard methodologies. The cDNA pools were transfected into CV1/EBNA cells and then incubated for 2 days with 1 μg/mL of B7L-1/Fc fusion protein. Following the B7L-1/Fc incubation period the cells were incubated with $^{125}$-labeled anti-human F(AB)$_2$. Autoradiographs were obtained and examined visually for positive cDNA pools having bound B7L-1/Fc. The positively identified pools were subdivided and rescreened. A single clone was identified that when retransfected into CV1/EBNA cells specifically bound the B7L-1/Fc fusion protein.

The clone, designated LDCAM, is described more fully in copending patent application Ser. No. 60/095,672 filed Aug. 7, 1998, which is incorporated herein by reference.

EXAMPLE 13

Immune System Cell Binding Studies

The following describes FACS cell binding experiments that demonstrate binding characteristics of B7L-1 and a protein for which it is a binding partner, LDCAM. Cells studied included murine T cells, human T cells, murine B cells, murine NK cells, human endothelial cells, and human tumor cell lines.

To study murine T cell binding, BALB/c murine lymph node (LN) cells were cultured in culture medium alone and in the presence of different stimuli for 18–20 hours. The cultured cells were harvested and prepared for binding studies using B7L1/Fc fusion protein, LDCAM/Fc fusion protein and a control Fc protein. Following an overnight culture BALB/c murine LN cells are typically >90% CD3+. Bound protein was detected using flow cytometric analysis. The results shown in Table I indicate observed binding expressed as mean fluorescence intensity units (MFI) on unstimulated T cells (medium) and on stimulated T cells (by stimuli).

TABLE I

| Fc | medium | Con A | TCR mAb | PHA |
|---|---|---|---|---|
| control Fc | 12.7 | 10.4 | 14.5 | 14.2 |
| B7L1Fc | 11.7 | 14.3 | 24.0 | 12.6 |
| LDCAM Fc | 18.7 | 51.7 | 230.0 | 91.4 |

When analyzed by T cell subsets, 75–80% of LN CD4+ murine T cells displayed detectable LDCAM binding after anti-TCR stimulation in vitro. About 50% of LN CD8+ murine T cells display detectable binding. In addition, CD4+ T cells exhibit higher levels of LDCAM binding than do CD8+ murine T cells. The results demonstrate that LDCAM/Fc binds at low levels to naïve T cells. However, after an overnight activation with polyclonal stimuli binding increased 5–20 fold depending on the stimuli. Of the stimuli studied PMA induces the least LDCAM binding to murine T cells, and anti-TCR induces the highest binding.

To study human T cells binding to LDCAM and its counterstructure, B7L1, human peripheral blood (PB) T cells were cultured in culture medium only or in the presence of different stimuli for 18–20 hours. The cultured cells were harvested and prepared for binding studies using either B7L/1Fc fusion protein, LDCAM/Fc fusion protein and a control Fc protein. Bound protein on the human PB T cells was determined by flow cytometric analysis. Table II details results observed, expressed as MFI, on unstimulated T cells (medium) and on stimulated T cells (by stimuli).

TABLE II

| Fc | medium | Con A | PMA | PHA |
|---|---|---|---|---|
| control Fc | 4.7 | 4.8 | 3.5 | 4.3 |
| B7L1Fc | 6.3 | 7.5 | 4.5 | 5.7 |
| LDCAM Fc | 22.3 | 42.8 | 61.9 | 38.8 |

The results show that, PMA induces greater LDCAM binding on human T cells than it does on murine T cells. The presence of specific binding of LDCAM to both murine and human T cells in the absence of B7L1 binding suggests that LDCAM is binding to B7L1, or a different molecule and not to itself. Because studies indicate that T cells express little or no B7L1, LDCAM may have another binding partner.

Studies similar to those described above were performed to evaluate LDCAM and B7L1 binding to murine splenic B cells. Neither B7L1 nor LDCAM binding was detected on unstimulated murine B cells. Culturing murine splenic B cells with muCD40L or LPS induced low levels of LDCAM binding but no appreciable level of B7L1 binding was detected.

In order to study binding to murine NK cells, spleens were removed from IL-15 treated CB-17/SCID mice and used as a source for highly enriched and activated murine NK cells. Spleen cells isolated from IL-15 treated SCID mice are 60–80% DX-5 positive. DX-5 is a pan NK marker than is expressed on NK cells from many different strains of mice. Flow cytometric analysis was performed as described above to detect B7L1 and LDCAM binding to DX-5+ in vivo IL-15 activated murine NK cells. Table II gives the results of a binding murine NK cell binding study.

TABLE III

| Fc molecule | DX-5 + NK cell % +/MFI |
|---|---|
| control Fc | 8%/88 |
| B7L1Fc | 19%/265 |
| LDCAM Fc | 38%/432 |

In contrast to that which was observed on murine and human T cells, LDCAM and B7L1 binding can be detected on in vivo activated murine NK cells.

Results of experiments directed at studying B7L1 and LDCAM binding to human endothelial cells demonstrated no binding on human umbilical vein endothelial cells (HUVEC) from different donors. However, one HUVEC from one donor B7L1 did induce low levels of CD62E and CD106 compared to control Fc.

Table IV details the results of experiments directed at evaluating B7L1 and LDCAM binding to human tumor cell lines. The results are expressed as percentage of cells binding LDCAM or B7L1.

Table IV

| Cell line | Cell type | LDCAMFc (% +)** | B7L1Fc (% +)** |
|---|---|---|---|
| U937 | monocytic leukemia | 10 | 7 |
| K562 | erythroblastic leukemia | 7 | 5 |
| Jurkat | acute T cell leukemia | 10 | 7 |
| MP-1 | B-cell LCL | 46 | 10 |
| DAUDI-hi | B-cell Burkitt's | 8 | 6 |
| RPMI 8866 | B-cell lymphoma | 0 | 0 |
| #88 EBV | B-cell LCL | 4 | 3 |
| #33 EBV | B-cell LCL | 0 | 0 |
| Tonsil G EBV | B-cell LCL | 25 | 13 |
| MDA231 | breast adenocarcinoma | 8 | 9 |
| OVCAR-3 | ovarian carcinoma | 48 | 30 |
| H2126M1 | lung adenocarcinoma | 0 | 0 |

**binding of control Fc has been subtracted out so this is net % + cells binding over background The results show significant LDCAM binding on ovarian carcinoma cell line and 2 of the human B-cell tumor lines (MP-1 and Tonsil G). B7L1 also binds to these three tumor cell lines but a much lower levels. These results demonstrate that LDCAM is a marker for certain types of B cell lymphomas or different types of carcinomas. In addition, biological signaling mediated by LDCAM or B7L1 could mediate functional anti tumor effects on these types of tumors.

What is claimed is:

1. An isolated polypeptide selected from the group consisting of:
   (a) a polypeptide comprising the amino acid sequence as set forth in SEQ ID NO:2; and
   (b) a polypeptide comprising amino acids $x_1$ to 364 of SEQ ID NO:2, wherein $x_1$ is 1 or 21.

2. The isolated polypeptide of claim 1, wherein $x_1$ is 21.

3. A composition comprising:
   an isolated polypeptide selected from the group consisting of:
   (a) a polypeptide comprising the amino acid sequence as set forth in SEQ ID NO:2; and
   (b) a polypeptide comprising amino acids $x_1$ to 364 of SEQ ID NO:2, wherein $x_1$ is 1 or 21,
   and an agent selected from the group consisting of a therapeutic drug, a toxin, a radionuclide, a chromophore, a colorometric molecule, and a fluorometric molecule,
   wherein the agent is linked to the polypeptide.

4. An isolated polypeptide encoded by DNA selected from the group consisting of:
   (a) a DNA comprising the nucleotide sequence as set forth in SEQ ID NO:1;
   (b) a DNA comprising the nucleotide sequence from $x_1$ to 1452 of SEQ ID NO:1, wherein $x_1$ is 157 or 217; and
   (c) a DNA comprising the nucleotide sequence from 108 to 1249 of SEQ ID NO:1.

5. A fusion polypeptide comprising the amino acid sequence from $x_1$ to 364 of SEQ ID NO:2, wherein $x_1$ is 1 or 21.

6. The fusion polypeptide of claim 5, wherein $x_1$ is 21.

7. The fusion polypeptide of claim 5, wherein the fusion polypeptide comprises an Fc region and/or a peptide linker.

8. A polypeptide produced by a method comprising culturing a recombinant host cell that has been transfected or transformed with a DNA selected from the group consisting of:
   (a) a DNA comprising the sequence as set forth in SEQ ID NO:1;
   (b) a DNA comprising the nucleotide sequence from $x_1$ to 1452 of SEQ ID NO:1, wherein $x_1$ is 157 or 217; and
   (c) a DNA comprising the nucleotide sequence from 108 to 1249 of SEQ ID NO:1,
   under conditions such that the polypeptide is produced from the DNA.

9. The polypeptide of claim 8, wherein $x_1$ is 157.

10. The polypeptide of claim 8, wherein $x_1$ is 217.

11. The polypeptide of claim 8, wherein the method further comprises recovering the polypeptide.

12. An isolated polypeptide selected from the group consisting of:
    (a) a polypeptide comprising the sequence as set forth in SEQ ID NO:4; and
    (b) a polypeptide comprising the sequence from about $x_1$ to 330 of SEQ ID NO:4, wherein $x_1$ is 1 or 21.

13. The isolated polypeptide of claim 12, wherein $x_1$ is 21.

14. An isolated polypeptide encoded by DNA selected from the group consisting of:
    (a) a DNA comprising the sequence as set forth in SEQ ID NO:3; and
    (b) a DNA comprising the sequence from nucleotide $x_2$ to 1206 of SEQ ID NO:3, wherein $x_2$ is 13 or 73.

15. The isolated polypeptide of claim 14, wherein the DNA comprises the sequence as set forth in SEQ ID NO: 3.

16. A fusion polypeptide comprising the amino acid sequence from $x_1$ to 330 of SEQ ID NO:4, wherein $x_1$ is 1 or 21.

17. The fusion protein of claim 16, wherein the fusion polypeptide comprises the sequence as set forth in SEQ ID NO:4 from amino acid 21 to amino acid 330.

18. The fusion polypeptide of claim 16, wherein the fusion polypeptide comprises an Fc region and/or a peptide linker.

19. A polypeptide produced by a method comprising culturing a recombinant host cell that has been transformed or transfected with a DNA selected from the group consisting of:
    (a) a DNA comprising the sequence as set forth in SEQ ID NO:3; and
    (b) a DNA comprising the nucleotide sequence $x_2$ to 1206 of SEQ ID NO:3, wherein $x_2$ is 13 or 73,
    wherein the host cell is cultured under conditions such that the polypeptide is produced from the DNA.

20. The polypeptide of claim 19, wherein $x_2$ is 13.

21. The polypeptide of claim 19, wherein $x_2$ is 73.

22. The polypeptide of claim 19, wherein the method further comprises recovering the polypeptide.

23. A composition comprising a suitable carrier and a polypeptide of claim 1.

24. A composition comprising a suitable carrier and a polypeptide of claim 12.

25. A composition comprising a suitable carrier and a fusion polypeptide of claim 5.

26. An isolated polypeptide comprising a B7L-1 variant consisting of a sequence as set forth from $x_1$ to X2 of SEQ ID NO: 2 having one amino acid deletion, insertion or substitution thereto, wherein $x_1$ is 1 or 21 and $x_2$ is 364 or 432, and wherein the B7L-1 variant is capable of binding a LDCAM polypeptide having a sequence as set forth in SEQ ID NO: 20 or 22.

27. An isolated polypeptide comprising a B7L-1 variant consisting of a sequence as set forth from $x_1$ to $x_2$ of SEQ ID NO: 2 having a deletion of 1 to 5 terminally located amino acids, wherein $x_1$ is 1 or 21 and $X_2$ is 364 or 432, and wherein the B7L-1 variant is capable of binding a LDCAM polypeptide having a sequence as set forth in SEQ ID NO: 20 or 22.

* * * * *